United States Patent
Gao et al.

(10) Patent No.: US 10,400,248 B2
(45) Date of Patent: Sep. 3, 2019

(54) DROUGHT TOLERANT PLANTS AND RELATED COMPOSITIONS AND METHODS INVOLVING GENES ENCODING DN-DTP1 POLYPEPTIDE

(71) Applicant: PIONEER OVERSEAS CORPORATION, Johnston, IA (US)

(72) Inventors: Yang Gao, Beijing (CN); Junhua Liu, Beijing (CN); Min Liu, Beijing (CN); Guihua Lu, Beijing (CN); Changgui Wang, Beijing (CN); Xiping Wang, Beijing (CN); Mian Xia, Beijing (CN); Kun Yu, Beijing (CN)

(73) Assignee: PIONEER OVERSEAS CORPORATION

( * ) Notice: Subject to any disclaimer, the term of this patent is extended or adjusted under 35 U.S.C. 154(b) by 102 days.

(21) Appl. No.: 15/104,271

(22) PCT Filed: Dec. 17, 2014

(86) PCT No.: PCT/CN2014/094028
§ 371 (c)(1),
(2) Date: Jun. 14, 2016

(87) PCT Pub. No.: WO2015/096646
PCT Pub. Date: Jul. 2, 2015

(65) Prior Publication Data
US 2016/0319296 A1      Nov. 3, 2016

(30) Foreign Application Priority Data
Dec. 24, 2013  (CN) .......................... 2013 1 0723667

(51) Int. Cl.
*A01H 1/00*       (2006.01)
*A01H 5/00*       (2018.01)
*C12N 15/00*      (2006.01)
*C12N 15/82*      (2006.01)
*C07K 14/415*     (2006.01)

(52) U.S. Cl.
CPC ........ *C12N 15/8273* (2013.01); *C07K 14/415* (2013.01)

(58) Field of Classification Search
None
See application file for complete search history.

(56) References Cited

U.S. PATENT DOCUMENTS

2008/0114160 A1 * 5/2008 Boukharov .......... C07K 14/415
536/23.6

FOREIGN PATENT DOCUMENTS

WO      2011/053897 A1    5/2011

OTHER PUBLICATIONS

Tanaka et al., UniProt Database, Acc. No. Q0JES3, Nucleic Acids Res. 36:D1028-D1033, 2008.*
International Search Report for PCT/CN2014/081601 dated Feb. 27, 2015.
Tanaka, Accession NM_001068989, *Oryza sativa* Japonica Group 0s08g0552200, Jun. 8, 2010.

* cited by examiner

*Primary Examiner* — Phuong T Bui

(57) ABSTRACT

Isolated polynucleotides and polypeptides, and recombinant DNA constructs useful for conferring drought tolerance; compositions (such as plants or seeds) comprising these recombinant DNA constructs; and methods utilizing these recombinant DNA constructs. The recombinant DNA constructs comprise polynucleotides operably linked to promoters that are functional in a plant, wherein said polynucleotides encode DN-DTP1 polypeptide.

Figure 1:
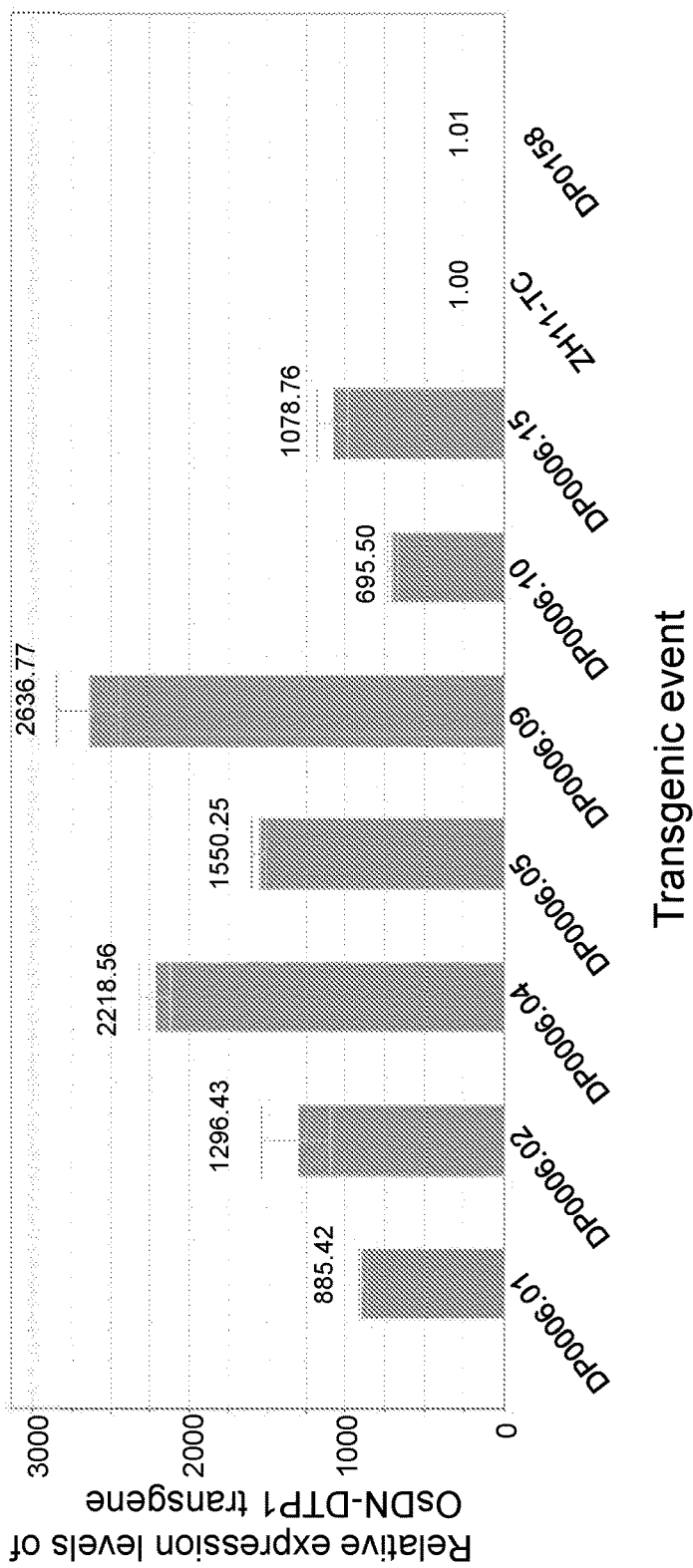

5 Claims, 3 Drawing Sheets
Specification includes a Sequence Listing.

DROUGHT TOLERANT PLANTS AND RELATED COMPOSITIONS AND METHODS INVOLVING GENES ENCODING DN-DTP1 POLYPEPTIDE

CROSS-REFERENCE TO RELATED APPLICATIONS

This application is a 35 U.S.C. § 371 National Stage PCT Application Ser. No. PCT/CN2014/094028, filed Dec. 17, 2017, which claims priority to CN201310723667, filed Dec. 24, 2013.

FIELD

The field relates to plant breeding and genetics and, in particular, relates to recombinant DNA constructs useful in plants for conferring tolerance to drought.

BACKGROUND

Stresses to plants may be caused by both biotic and abiotic agents. For example, biotic causes of stress include infection with pathogen, insect feeding, and parasitism by another plant such as mistletoe. Abiotic stresses include, for example, excessive or insufficient available water, temperature extremes, and synthetic chemicals such as herbicides.

Abiotic stress is the primary cause of crop loss worldwide, causing average yield losses more than 50% for major crops (Boyer, J. S. (1982) Science 218:443-448; Bray, E. A. et al. (2000) In Biochemistry and Molecular Biology of Plants, edited by Buchannan, B. B. et al., Amer. Soc. Plant Biol., pp. 1158-1249). Among the various abiotic stresses, drought is the major factor that limits crop productivity worldwide, and exposure of plants to a water-limiting environment during various developmental stages appears to activate various physiological and developmental changes. Although many reviews on molecular mechanisms of abiotic stress responses and genetic regulatory networks of drought stress tolerance have been published (Valliyodan, B., and Nguyen, H. T. (2006) Curr. Opin. Plant Biol. 9:189-195; Wang, W., et al. (2003) Planta 218:1-14; Vinocur, B., and Altman, A. (2005) Curr. Opin. Biotechnol. 16:123-132; Chaves, M. M., and Oliveira, M. M. (2004) J. Exp. Bot. 55:2365-2384; Shinozaki, K., et al. (2003) Curr. Opin. Plant Biol. 6:410-417; Yamaguchi-Shinozaki, K., and Shinozaki, K. (2005) Trends Plant Sci. 10:88-94), it is also a major challenge in biology to understand the basic biochemical and molecular mechanisms for drought stress perception, transduction and tolerance.

Earlier work on molecular aspects of abiotic stress responses was accomplished by differential and/or subtractive analysis (Bray, E. A. (1993) Plant Physiol. 103:1035-1040; Shinozaki, K., and Yamaguchi-Shinozaki, K. (1997) Plant Physiol. 115:327-334; Zhu, J.-K. et al. (1997) Crit. Rev. Plant Sci. 16:253-277; Thomashow, M. F. (1999) Annu. Rev. Plant Physiol. Plant Mol. Biol. 50:571-599); and other methods which include selection of candidate genes and analysis of expression of such a gene or its active product under stresses, or by functional complementation in a stressor system that is well defined (Xiong, L. and Zhu, J.-K. (2001) Physiologia Plantarum 112:152-166). Additionally, forward and reverse genetic studies involving the identification and isolation of mutations in regulatory genes have been used to provide evidence for observed changes in gene expression under stress (Xiong, L. and Zhu, J.-K. (2001) Physiologia Plantarum 112:152-166).

Activation tagging can be utilized to identify genes with the ability to affect a trait, and this approach has been used in Arabidopsis thaliana (the model plant species) (Weigel, D., et al. (2000) Plant Physiol. 122:1003-1013). Insertions of transcriptional enhancer elements can dominantly activate and/or elevate the expression of nearby endogenous genes, so this method can be used to select genes involved in agronomically important phenotypes, including abiotic stress tolerance such as improved drought tolerance.

SUMMARY

The following embodiments are among those encompassed by the disclosure:

1. An isolated polynucleotide comprising: (a) a nucleotide sequence encoding a polypeptide with an amino acid sequence of at least 90% sequence identity to SEQ ID NO: 4; or (b) a nucleotide sequence of SEQ ID NO: 2; or (c) a nucleotide sequence of SEQ ID NO: 3; or (d) a nucleotide sequence having at least 85% identity with the full length nucleotide sequence of (a) or (b) or (c); or (e) a full complement of the nucleotide sequence of (a) or (b) or (c) or (d), wherein the full complement and the nucleotide sequence consist of the same number of nucleotides and are 100% complementary, overexpression of the polynucleotide in a plant enhances drought tolerance. The isolated polynucleotide encoded a polypeptide comprising the amino acid sequence of SEQ ID NO: 4. The nucleotide sequence may comprise the nucleotide sequence of SEQ ID NO: 2 or SEQ ID NO: 3.

2. A recombinant DNA construct comprising the isolated polynucleotide of embodiment 1 operably linked to at least one heterologous regulatory sequence.

3. A transgenic plant comprising in its genome a recombinant DNA construct comprising a polynucleotide operably linked to at least one heterologous regulatory element, wherein said polynucleotide encodes a DN-DTP1 (an expressed protein) polypeptide having an amino acid sequence of at least 85% sequence identity to SEQ ID NO: 4, and wherein said transgenic plant exhibits increased drought tolerance and/or paraquat tolerance when compared to a control plant.

4. A transgenic plant comprising in its genome a recombinant DNA construct comprising a polynucleotide operably linked to at least one regulatory element, wherein said polynucleotide encodes a polypeptide having an amino acid sequence of at least 85% sequence identity to SEQ ID NO: 4, and wherein said plant exhibits an alteration of at least one agronomic characteristics when compared to a control plant. Optionally, the plant exhibits said alteration of said at least one agronomic characteristics when compared, under water limiting conditions, to a control plant. The at least one agronomic trait may be grain yield or biomass, and the alteration may be an increase.

5. A transgenic plant of embodiment 3 or 4, wherein the plant is selected from the group consisting of: rice, maize, soybean, sunflower, sorghum, canola, wheat, alfalfa, cotton, barley, millet, sugarcane and switchgrass.

6. Seed of the transgenic plant of embodiment 3 or 4 or 5, wherein said seed comprises in its genome a recombinant DNA construct comprising a polynucleotide operably linked to at least one regulatory element, wherein said polynucleotide encodes a polypeptide having an amino acid sequence of at least 85% sequence identity, when compared to SEQ ID NO: 4, and wherein a transgenic plant produced from said seed exhibits an increased drought tolerance, or an alteration of at least one other agronomic characteristics, or both, when compared to a control plant. The at least one other agronomic trait may be grain yield, biomass, or a combination, and the alteration may be an increase.

7. A method of increasing drought tolerance in a plant, comprising: (a) introducing into a regenerable plant cell a recombinant DNA construct comprising a polynucleotide operably linked to at least one regulatory sequence, wherein the polynucleotide encodes a polypeptide having an amino acid sequence of at least 85% sequence identity to SEQ ID NO: 4; (b) regenerating a transgenic plant from the regenerable plant cell after step (a), wherein the transgenic plant comprises in its genome the recombinant DNA construct; and (c) obtaining a progeny plant derived from the transgenic plant of step (b), wherein said progeny plant comprises in its genome the recombinant DNA construct and exhibits increased drought tolerance when compared to a control plant.

8. A method of improving drought tolerance also comprising: (a) crossing the plant of embodiment 3 or 4 or 5 with a second plant to produce progeny seed; (b) harvesting and planting the progeny seed to produce at least one progeny plant of a subsequent generation, wherein said progeny plant comprises in its genome the recombinant DNA construct of embodiment 3; (c) crossing the progeny plant with the second plant to produce at least one backcross progeny seed; and optionally; (d) repeating steps (b) and (c) for additional generations to produce a plant with improved drought tolerance when compared to the second plant.

9. A method of evaluating drought tolerance in a plant, comprising: (a) obtaining a transgenic plant, wherein the transgenic plant comprises in its genome a recombinant DNA construct comprising a polynucleotide operably linked to at least one regulatory element, wherein said polynucleotide encodes a polypeptide having an amino acid sequence of at least 85% sequence identity to SEQ ID NO: 4; (b) obtaining a progeny plant derived from the transgenic plant, wherein the progeny plant comprises in its genome the recombinant DNA construct; and (c) evaluating the progeny plant for drought tolerance compared to a control plant.

10. A method of determining an alteration of at least one agronomic characteristics in a plant, comprising: (a) obtaining a transgenic plant, wherein the transgenic plant comprises in its genome a recombinant DNA construct comprising a polynucleotide operably linked to at least one regulatory element, wherein said polynucleotide encodes a polypeptide having an amino acid sequence of at least 85% sequence identity to SEQ ID NO: 4, wherein the transgenic plant comprises in its genome the recombinant DNA construct; (b) obtaining a progeny plant derived from the transgenic plant, wherein the progeny plant comprises in its genome the recombinant DNA construct; and (c) determining whether the progeny plant exhibits an alteration of at least one agronomic characteristics when compared to a control plant. Optionally, said determining step (c) comprises determining whether the transgenic plant exhibits an alteration of at least one agronomic characteristic when compared, under water limiting conditions, to a control plant. The at least one agronomic trait may be grain yield, biomass, or a combination, and the alteration may be an increase.

11. Any of the methods of the embodiments 7-10, wherein the plant is selected from the group consisting of: rice, maize, soybean, sunflower, sorghum, canola, wheat, alfalfa, cotton, barley, millet, sugarcane and switchgrass.

12. A rice transgenic plant comprising a recombinant transcriptional activator element enhancing the expression of an endogenous polynucleotide, wherein the polynucleotide encodes an amino acid sequence that is 90% identical to SEQ ID NO: 4.

13. A method of increasing drought tolerance of a rice plant in a field, the method comprising (a) expressing a recombinant nucleic acid encoding a rice DN-DTP1 polypeptide in a rice plant; (b) growing the rice plant under crop growing conditions in the field, wherein the rice plant is exposed to drought conditions; and (c) increasing the drought tolerance of the rice plant.

14. A method of increasing yield of a rice plant in a field, the method comprising (a) expressing a recombinant nucleic acid encoding a rice DN-DTP1 polypeptide in a rice plant; (b) growing the rice plant under crop growing conditions in the field, wherein the rice plant is exposed to drought conditions; and (c) increasing the grain yield of the rice plant.

15. A method of identifying an allele of OsDN-DTP1 gene that results in an increased expression or activity of the OsDN-DTP1 polypeptide, the method comprising the steps of: (a) performing a genetic screen on a population of mutant plants; (b) identifying one or more mutant plants that exhibit the increased expression or activity of the OsDN-DTP1 polypeptide or a homolog thereof; and (c) identifying the OsDN-DTP1 allele or a homolog thereof from the mutant plant.

16. A method of screening for alleles of OsDN-DTP1, the method comprising (a) sequencing one or more genomic DNA fragments isolated from one or more rice populations with an oligonucleotide primer targeted to the OsDN-DTP1 gene; (b) analyzing the differences of the DNA sequence in the regulatory or the coding region of the OsDN-DTP1 gene; and (c) correlating an allele of OsDN-DTP1 with increased drought tolerance or yield.

17. A rice transgenic plant, comprising in its genome a recombinant construct that results in an increased expression of OsDN-DTP1 polypeptide, wherein the polypeptide comprises SEQ ID NO:4.

In another embodiment, the present disclosure concerns a recombinant DNA construct comprising any of the isolated polynucleotides of the present disclosure operably linked to at least one regulatory sequence, and a cell, a plant, or a seed comprising the recombinant DNA construct. The cell may be eukaryotic, e.g., a yeast, insect or plant cell; or prokaryotic, e.g., a bacterial cell.

BRIEF DESCRIPTION OF THE DRAWINGS AND SEQUENCE LISTING

The disclosure can be more fully understood from the following detailed description and the accompanying drawings and sequence listing which form a part of this application.

FIG. 1 provides relative expression levels of OsDN-DTP1 transgene in leaves of separate transgenic rice events by real-time PCR analyses. The base level of expression in ZH11-TC was set at 1.00, and the expression levels in OsDN-DTP1 events were shown as fold-increases compared to ZH11-TC.

Figure 2:
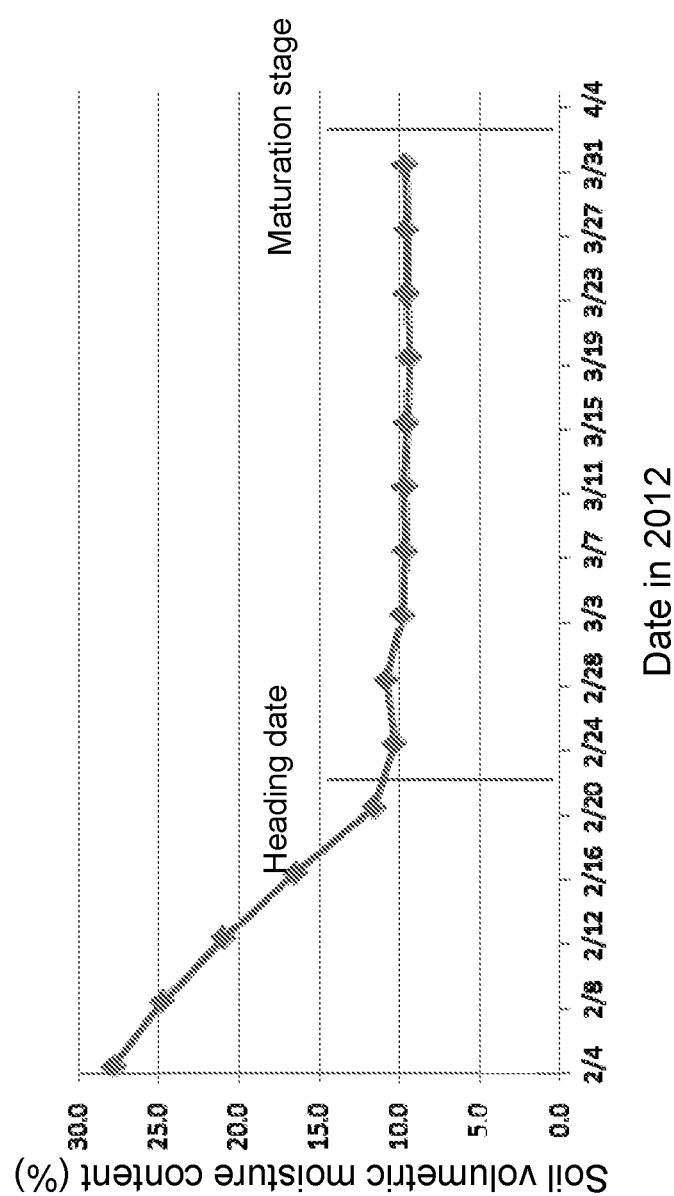

FIG. 2 shows changes of soil volumetric moisture content at different developmental stage in Hainan field in a growing season.

Figure 3:
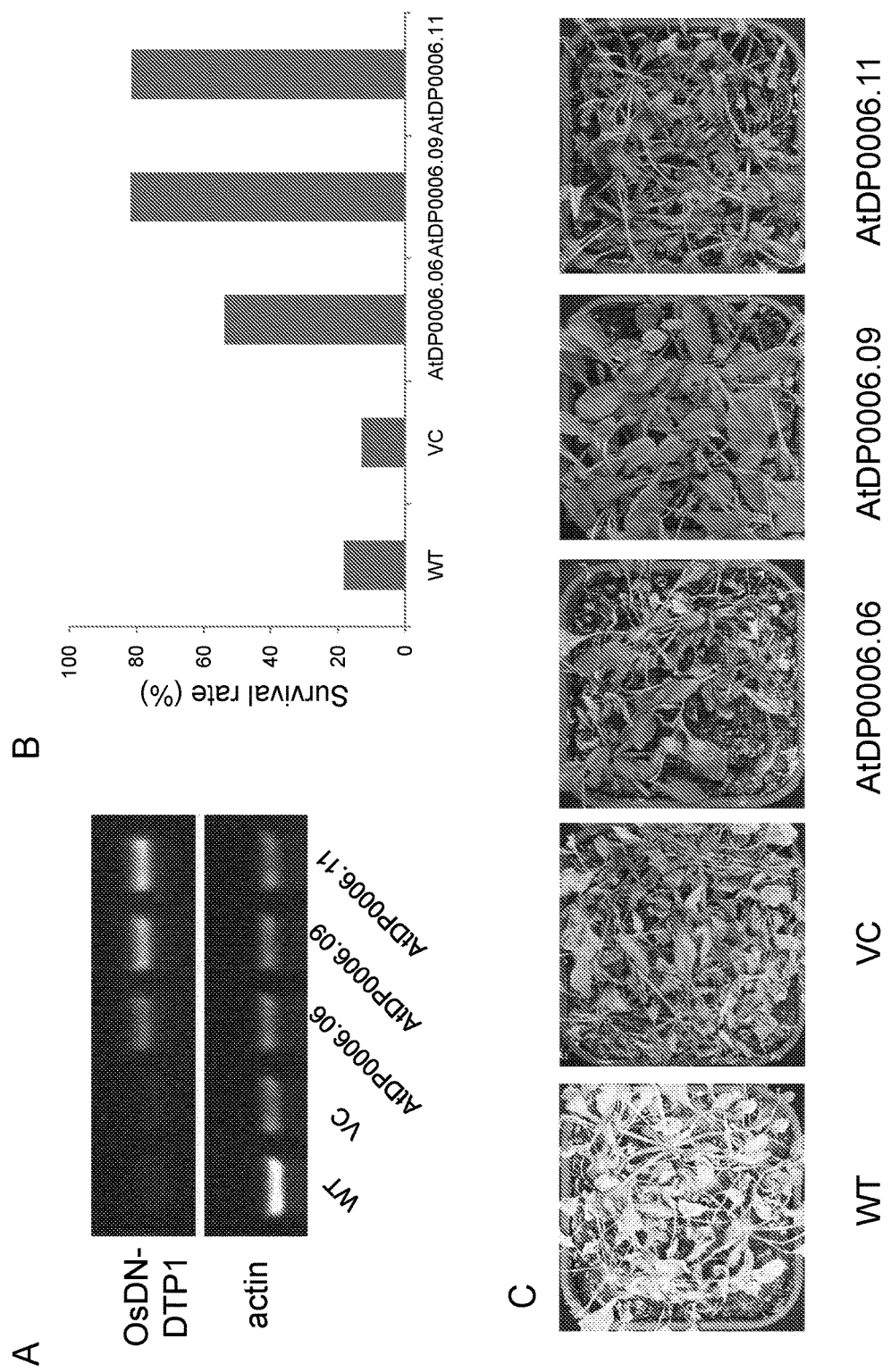

FIG. 3 provides photographs and figures indicating that overexpression of rice OsDN-DTP1 gene under CaMV 35S promoter in *Arabidopsis* (events AtDP0006.06, AtDP0006.09, AtDP0006.11) can significantly increase drought tolerance. A. semi-quantitative PCR analysis of OsDN-DTP1 gene in transgenic *Arabidopsis*; B. Survival rate on the 3$^{rd}$ day after re-watering; and C. photographs taken on the 3$^{rd}$ day after re-watering. WT, wild type Columbia; VC, Enpty vector DP0009 transformant.

Table 1. SEQ ID NOs for nucleotide and amino acid sequences provided in the sequence listing Table 2. Drought tolerance assays of AH00838 plants at T$_1$ generation under greenhouse conditions Table 3. Drought tolerance assays of AH00838 plants at T$_2$ generation under greenhouse conditions Table 4. Grain yield assay of OsDN-DTP1-rice plants at T$_2$ generation under field drought conditions Table 5. Paraquat tolerance assay of OsDN-DTP1-transgenic rice plants at T$_2$ generation at transgenic event level (1$^{st}$ experiment) Table 6. Paraquat tolerance assay of OsDN-DTP1-transgenic rice plants at T$_2$ generation at transgenic event level (2$^{nd}$ experiment)

TABLE 1

SEQ ID NOs for nucleotide and amino acid sequences provided in the sequence listing

| Source species | Clone Designation | SEQ ID NO: (Nucleotide) | SEQ ID NO: (Amino Acid) |
|---|---|---|---|
| *Oryza sativa* | T-DNA flanking sequence in AH00838 tagging line (RB) | 1 | n/a |
| *Oryza sativa* | OsDN-DTP1 | 2, 3 | 4 |
| Artificial | Primers | 5-18 | n/a |

The Sequence Listing contains the one-letter code for nucleotide sequences and the three-letter code for amino acid sequences as defined in conformity with the IUPAC-IUBMB standards described in *Nucleic Acids Res.* 13:3021-3030 (1985) and in the *Biochemical J.* 219 (No. 2):345-373 (1984) which are herein incorporated by reference. The symbols and format used for nucleotide and amino acid sequence data comply with the rules set forth in 37 C.F.R. § 1.822.

DETAILED DESCRIPTION

The disclosure of each reference set forth herein is hereby incorporated by reference in its entirety.

As used herein and in the appended claims, the singular forms "a", "an", and "the" include plural reference unless the context clearly dictates otherwise. Thus, for example, reference to "a plant" includes a plurality of such plants; reference to "a cell" includes one or more cells and equivalents thereof known to those skilled in the art, and so forth.

As used herein:

The term "OsDN-DTP1" refers to a rice protein that confers a drought tolerance and/or paraquat tolerance phenotype and is encoded by the rice gene locus OS04g0208800. The terms "DTP" and "Drought Tolerance Phenotype" are used interchangeably herein. "DTP1 polypeptide" refers to a protein with a Drought Tolerance Phenotype and refers herein to the OsDN-DTP1 polypeptide and its homologs from other organisms.

The OsDN-DTP1 polypeptide (SEQ ID NO: 4) is encoded by the nucleotide sequence (SEQ ID NO: 3) at rice gene locus Os04g0208800. This protein does not have any prior assigned function or annotation.

The terms "monocot" and "monocotyledonous plant" are used interchangeably herein. A monocot of the current disclosure includes plants of the Gramineae family.

The terms "dicot" and "dicotyledonous plant" are used interchangeably herein. A dicot of the current disclosure includes the following families: Brassicaceae, Leguminosae, and Solanaceae.

The terms "full complement" and "full-length complement" are used interchangeably herein, and refer to a complement of a given nucleotide sequence, wherein the complement and the nucleotide sequence consist of the same number of nucleotides and are 100% complementary.

An "Expressed Sequence Tag" ("EST") is a DNA sequence derived from a cDNA library and therefore represents a sequence which has been transcribed. An EST is typically obtained by a single sequencing pass of a cDNA insert. The sequence of an entire cDNA insert is termed the "Full-Insert Sequence" ("FIS"). A "Contig" sequence is a sequence assembled from two or more sequences that can be selected from, but not limited to, the group consisting of an EST, FIS and PCR sequence. A sequence encoding an entire or functional protein is termed a "Complete Gene Sequence" ("CGS") and can be derived from an FIS or a contig.

The term "trait" refers to a physiological, morphological, biochemical, or physical characteristics of a plant or particular plant material or cell. In some instances, this characteristics is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar or nitrogen concentrations, or by the observation of the expression level of a gene or genes, or by agricultural observations such as osmotic stress tolerance or yield.

"Agronomic characteristics" is a measurable parameter including but not limited to: greenness, grain yield, growth rate, total biomass or rate of accumulation, fresh weight at maturation, dry weight at maturation, fruit yield, grain yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress.

Increased biomass can be measured, for example, as an increase in plant height, plant total leaf area, plant fresh weight, plant dry weight or plant grain yield, as compared with control plants.

The ability to increase the biomass or size of a plant would have several important commercial applications. Crop cultivars may be developed to produce higher yield of the vegetative portion of the plant, to be used in food, feed, fiber, and/or biofuel.

Increased leaf size may be of particular interest. Increased leaf biomass can be used to increase production of plant-derived pharmaceutical or industrial products. Increased tiller number may be of particular interest and can be used to increase yield. An increase in total plant photosynthesis is typically achieved by increasing leaf area of the plant. Additional photosynthetic capacity may be used to increase the yield derived from particular plant tissue, including the leaves, roots, fruits or seed, or permit the growth of a plant under decreased light intensity or under high light intensity.

Modification of the biomass of another tissue, such as root tissue, may be useful to improve a plant's ability to grow under harsh environmental conditions, including drought or nutrient deprivation, because larger roots may better reach or take up water or nutrients.

For some ornamental plants, the ability to provide larger varieties would be highly desirable. For many plants, including fruit-bearing trees, trees that are used for lumber production, or trees and shrubs that serve as view or wind screens, increased stature provides improved benefits, such as in the forms of greater yield or improved screening.

"Transgenic" refers to any cell, cell line, callus, tissue, plant part or plant, the genome of which has been altered by the presence of a heterologous nucleic acid, such as a recombinant DNA construct. The term "transgenic" used herein includes those initial transgenic events as well as those created by sexual crosses or asexual propagation from the initial transgenic event, and does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A "control" or "control plant" or "control plant cell" provides a reference point for measuring changes in phenotype of a subject plant or plant cell which was genetically altered by, such as transformation, and has been affected as to a gene of interest. A subject plant or plant cell may be descended from a plant or cell so altered and will comprise the alteration.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to a condition or stimulus that would induce expression of the gene of interest; or (e) the subject plant or plant cell itself, under conditions in which the gene of interest is not expressed.

In this disclosure, WT, ZH11-TC, VC, and CK indicate control plants. WT represents wild-type rice or *Arabidopsis* plants, ZH11-TC represents rice plants generated from tissue cultured Zhonghua11, VC represents plants transformed with empty vector of DP0005 or DP0009, and CK represents segregated null plants.

"Genome" as it applies to plant cells encompasses not only chromosomal DNA found within the nucleus, but also organelle DNA found within subcellular components (e.g., mitochondria, plastid) of the cell.

"Plant" includes reference to whole plants, plant organs, plant tissues, seeds and plant cells and progeny of the same. Plant cells include, without limitation, cells from seeds, suspension cultures, embryos, meristematic regions, callus tissues, leaves, roots, shoots, gametophytes, sporophytes, pollen, and microspores.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct. A $T_0$ plant is directly recovered from the transformation and regeneration process. Progeny of $T_0$ plants are referred to as $T_1$ (first progeny generation), $T_2$ (second progeny generation), etc.

"Heterologous" with respect to sequence means a sequence that originates from a foreign species, or, if from the same species, is substantially modified from its native form in composition and/or genomic locus by deliberate human intervention.

"Polynucleotide", "nucleic acid sequence", "nucleotide sequence", and "nucleic acid fragment" are used interchangeably and refer to a polymer of RNA or DNA that is single- or double-stranded, optionally containing synthetic, non-natural or altered nucleotide bases. Nucleotides (usually found in their 5'-monophosphate form) are referred to by their single-letter designation as follows: "A" for adenylate or deoxyadenylate, "C" for cytidylate or deoxycytidylate, and "G" for guanylate or deoxyguanylate for RNA or DNA, respectively; "U" for uridylate; "T" for deoxythymidylate; "R" for purines (A or G); "Y" for pyrimidines (C or T); "K" for G or T; "H" for A or C or T; "I" for inosine; and "N" for any nucleotide.

"Polypeptide", "peptide", "amino acid sequence" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The terms "polypeptide", "peptide", "amino acid sequence", and "protein" are also inclusive of modifications including, but not limited to, glycosylation, lipid attachment, and sulfation, gamma-carboxylation of glutamic acid residues, hydroxylation and ADP-ribosylation.

"Messenger RNA (mRNA)" refers to the RNA which has no intron and can be translated into protein by the cell.

"cDNA" refers to a DNA that is complementary to and synthesized from an mRNA template using reverse transcriptase. The cDNA can be single-stranded or converted into the double-stranded form using the Klenow fragment of DNA polymerase I.

"Mature" protein refers to a post-translationally processed polypeptide; i.e., any pre- or pro-peptides present in the primary translation product has been removed.

"Precursor" protein refers to the primary product of translation of mRNA; i.e., with pre- and pro-peptides still present. Pre- and pro-peptides may be and are not limited to intracellular localization signals.

"Isolated" refers to materials, such as nucleic acid molecules and/or proteins, which are substantially free or otherwise removed from components that normally accompany or interact with the materials in a naturally occurring environment. Isolated polynucleotides may be purified from a host cell in which they naturally occur. Conventional nucleic acid purification methods known to skilled artisans may be used to obtain isolated polynucleotides. The term also embraces recombinant polynucleotides and chemically synthesized polynucleotides.

"Recombinant" refers to an artificial combination of two otherwise separated segments of sequence, e.g., by chemical synthesis or by the manipulation of isolated segments of nucleic acids by genetic engineering techniques. "Recombinant" also includes reference to a cell or vector, that has been modified by the introduction of a heterogeneous nucleic acid or a cell derived from a cell so modified, but does not encompass the alteration of the cell or vector by naturally occurring events (e.g., spontaneous mutation, natural transformation/transduction/transposition) such as those occurring without deliberate human intervention.

"Recombinant DNA construct" refers to a combination of nucleic acid fragments that are not normally found together in nature. Accordingly, a recombinant DNA construct may comprise regulatory sequences and coding sequences that are derived from different sources, or regulatory sequences and coding sequences derived from the same source, but arranged in a manner different than that normally found in nature.

The terms "entry clone" and "entry vector" are used interchangeably herein.

"Regulatory sequences" refer to nucleotide sequences located upstream (5' non-coding sequences), within, or downstream (3' non-coding sequences) of a coding sequence, and influencing the transcription, RNA processing or stability, or translation of the associated coding sequence. Regulatory sequences may include, but are not limited to, promoters, translation leader sequences, introns, and polyadenylation recognition sequences. The terms "regulatory sequence" and "regulatory element" are used interchangeably herein.

"Promoter" refers to a nucleic acid fragment capable of controlling transcription of another nucleic acid fragment.

"Promoter functional in a plant" is a promoter capable of controlling transcription of genes in plant cells whether or not its origin is from a plant cell.

"Tissue-specific promoter" and "tissue-preferred promoter" may refer to a promoter that is expressed predominantly but not necessarily exclusively in one tissue or organ, but that may also be expressed in one specific cell or cell type.

"Developmentally regulated promoter" refers to a promoter whose activity is determined by developmental events.

"Operably linked" refers to the association of nucleic acid fragments in a single fragment so that the function of one is regulated by the other. For example, a promoter is operably linked with a nucleic acid fragment when it is capable of regulating the transcription of that nucleic acid fragment.

"Expression" refers to the production of a functional product. For example, expression of a nucleic acid fragment may refer to transcription of the nucleic acid fragment (e.g., transcription resulting in mRNA or functional RNA) and/or translation of mRNA into a precursor or mature protein.

"Phenotype" means the detectable characteristics of a cell or organism.

"Introduced" in the context of inserting a nucleic acid fragment (e.g., a recombinant DNA construct) into a cell, means "transfection" or "transformation" or "transduction" and includes reference to the incorporation of a nucleic acid fragment into an eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

A "transformed cell" is any cell into which a nucleic acid fragment (e.g., a recombinant DNA construct) has been introduced.

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation.

"Transient transformation" refers to the introduction of a nucleic acid fragment into the nucleus, or DNA-containing organelle, of a host organism resulting in gene expression without genetically stable inheritance.

An "allele" is one of two or more alternative forms of a gene occupying a given locus on a chromosome. When the alleles present at a given locus on a pair of homologous chromosomes in a diploid plant are the same, that plant is homozygous at that locus. If the alleles present at a given locus on a pair of homologous chromosomes in a diploid plant differ, that plant is heterozygous at that locus. If a transgene is present on only one of a pair of homologous chromosomes in a diploid plant, that plant is hemizygous at that locus.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels. (1991) *Ann. Rev. Plant Phys. Plant Mol. Biol.* 42:21-53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel. (1992) *Plant Phys.* 100:1627-1632). A "mitochondrial signal peptide" is an amino acid sequence which directs a precursor protein into the mitochondria (Zhang and Glaser. (2002) *Trends Plant Sci* 7:14-21).

Methods to determine the relationship of various polynucleotide and polypeptide sequences are known. As used herein, "reference sequence" is a defined sequence used as a basis for sequence comparison. A reference sequence may be a subset or the entirety of a specified sequence, such as a segment of a full-length cDNA or gene sequence, or may be the complete cDNA or gene sequence. As used herein, "comparison window" makes reference to a contiguous and specified segment of a polynucleotide or polypeptide sequence, wherein the sequence in the comparison window may comprise additions or deletions (i.e., gaps) compared to the reference sequence (which does not comprise additions or deletions) for optimal alignment of the two sequences. Generally, the comparison window is at least 20 contiguous nucleotides or amino acids in length, and optionally can be 30, 40, 50, 100 or longer. Those of skill in the art understand that to avoid a high similarity to a reference sequence due to inclusion of gaps in the sequence, a gap penalty is typically introduced and is subtracted from the number of matches.

The determination of percent sequence identity between any two sequences can be accomplished using a mathematical algorithm. Examples of such mathematical algorithms for sequence comparison include the algorithm of Myers and Miller. (1988) *CABIOS* 4:11-17; the local alignment algorithm of Smith, et al. (1981) *Adv. Appl. Math.* 2:482; the global alignment algorithm of Needleman and Wunsch. (1970) *J. Mol. Biol.* 48:443-453; the search-for-local alignment method of Pearson and Lipman. (1988) *Proc. Natl. Acad. Sci.* 85:2444-2448; the algorithm of Karlin and Altschul. (1990) *Proc. Natl. Acad. Sci. USA* 872264, modified as in Karlin and Altschul. (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package, Version 10 (available from Accelrys Inc., 9685 Scranton Road, San Diego, Calif., USA); and the Megalign® program of the LASERGENE® bioinformatics computing suite (DNASTAR® Inc., Madison, Wis.).

Alignments using these programs can be performed using the default parameters. The CLUSTAL program is well described by Higgins, et al. (1988) *Gene* 73:237-244; Higgins, et al. (1989) *CABIOS* 5:151-153; Corpet, et al. (1988) *Nucleic Acids Res.* 16:10881-10890; Huang, et al. (1992) *CABIOS* 8:155-165 and Pearson, et al. (1994) *Meth. Mol. Biol.* 24:307-331. The ALIGN program is based on the algorithm of Myers and Miller, (1988) supra. A PAM120 weight residue table, a gap length penalty of 12 and a gap penalty of 4 can be used with the ALIGN program when comparing amino acid sequences. The BLAST programs of Altschul, et al. (1990) *J. Mol. Biol.* 215:403 are based on the algorithm of Karlin and Altschul. (1990) supra. BLAST nucleotide searches can be performed with the BLASTN program, score=100, wordlength=12, to obtain nucleotide sequences homologous to a nucleotide sequence encoding a protein of the disclosures. BLAST protein searches can be performed with the BLASTX program, score=50, wordlength=3, to obtain amino acid sequences homologous to a protein or polypeptide of the disclosures. To obtain gapped alignments for comparison purposes, Gapped BLAST (in BLAST 2.0) can be utilized as described in Altschul, et al. (1997) *Nucleic Acids Res.* 25:3389. Alternatively, PSI-BLAST (in BLAST 2.0) can be used to perform an iterated search that detects distant relationships between molecules (Altschul, et al. (1997) supra). When utilizing BLAST, Gapped BLAST, PSI-BLAST and the default parameters of the respective programs (e.g., BLASTN for nucleotide sequences, BLASTX for proteins) can be used (the National Center for Biotechnology Information of the National Library of Medicine of the National Institutes of Health of the U.S. government). Alignment may also be performed by manual inspection.

Paired sequence identity/similarity values can be obtained using GAP Version 10 with the following parameters: % identity and % similarity for a nucleotide sequence using GAP Weight of 50 and Length Weight of 3 and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch. (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the Quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (Henikoff and Henikoff. (1989) *Proc. Natl. Acad. Sci. USA* 89:10915).

Unless stated otherwise, multiple alignments of the sequences provided herein are performed using the Clustal V method of alignment (Higgins and Sharp. (1989) *CABIOS.* 5:151-153) with the default parameters (GAP PENALTY=10, GAP LENGTH PENALTY=10). Default parameters for pairwise alignments and calculation of percent identity of amino acid sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

As used herein, "percentage of sequence identity" is calculated by determining the number of positions at which the identical nucleic acid base or amino acid residue occurs in both sequences to yield the number of matched positions, dividing the number of matched positions by the total number of positions in the window of comparison, and multiplying the result by 100.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Embodiments include isolated polynucleotides and polypeptides, and recombinant DNA constructs useful for conferring drought tolerance; compositions (such as plants or seeds) comprising these recombinant DNA constructs; and methods utilizing these recombinant DNA constructs.

Isolated Polynucleotides and Polypeptides:

The present disclosure includes the following isolated polynucleotides and polypeptides:

An isolated polynucleotide comprising: (i) a nucleic acid sequence encoding a polypeptide having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4; or (ii) a full complement of the nucleic acid sequence of (i), wherein the full complement and the nucleic acid sequence of (i) consist of the same number of nucleotides and are 100% complementary. Any of the foregoing isolated polynucleotides may be utilized in any recombinant DNA constructs of the present disclosure. Overexpression of the encoded polypeptide increases plant drought tolerance and/or paraquat tolerance activity.

An isolated polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4. The polypeptide is preferably an DN-DTP1 polypeptide. Overexpression of the polypeptide increases plant drought tolerance and/or paraquat tolerance activity.

An isolated polynucleotide comprising (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 3; or (ii) a full complement of the nucleic acid sequence of (i). Any of the foregoing isolated polynucleotides may be utilized in any recombinant DNA constructs of the present disclosure. The isolated polynucleotide preferably encodes a DN-DTP1 polypeptide. Overexpression of this polypeptide improves plant drought tolerance and/or paraquat tolerance activity.

Recombinant DNA Constructs:

In one aspect, the present disclosure includes recombinant DNA constructs.

In one embodiment, a recombinant DNA construct comprises a polynucleotide operably linked to at least one regulatory sequence (e.g., a promoter functional in a plant), wherein the polynucleotide comprises (i) a nucleic acid sequence encoding an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide comprises (i) a nucleic acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 3; or (ii) a full complement of the nucleic acid sequence of (i).

In another embodiment, a recombinant DNA construct comprises a polynucleotide operably linked to at least one regulatory sequence (e.g., a promoter functional in a plant), wherein said polynucleotide encodes a DN-DTP1 polypeptide. This polypeptide has drought tolerance and/or paraquat tolerance activity, and may be from, for example, *Oryza sativa*, *Oryza australiensis*, *Oryza barthii*, *Oryza glaberrima* (African rice), *Oryza latifolia*, *Oryza longistaminata*, *Oryza meridionalis*, *Oryza officinalis*, *Oryza punctata*, *Oryza rufipogon* (brownbeard or red rice), *Oryza nivara* (Indian wild rice), *Arabidopsis thaliana*, *Zea mays*, *Glycine max*, *Glycine tabacina*, *Glycine soja* or *Glycine tomentella*.

It is understood, as those skilled in the art will appreciate, that the disclosure encompasses more than the specific exemplary sequences. Alterations in a nucleic acid fragment which result in the production of a chemically equivalent amino acid at a given site, but do not affect the functional properties of the encoded polypeptide, are well known in the art. For example, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products.

Regulatory Sequences:

A recombinant DNA construct of the present disclosure may comprise at least one regulatory sequence.

A regulatory sequence may be a promoter.

A number of promoters can be used in recombinant DNA constructs of the present disclosure. The promoters can be selected based on the desired outcome, and may include constitutive, tissue-specific, inducible, or other promoters for expression in the host organism.

Promoters that cause a gene to be expressed in most cell types at most times are commonly referred to as "constitutive promoters".

High-level, constitutive expression of the candidate gene under control of the 35S or UBI promoter may have pleiotropic effects, although candidate gene efficacy may be estimated when driven by a constitutive promoter. Use of tissue-specific and/or stress-induced promoters may eliminate undesirable effects but retain the ability to enhance drought tolerance. This effect has been observed in *Arabidopsis* (Kasuga et al. (1999) *Nature Biotechnol.* 17:287-91).

Suitable constitutive promoters for use in a plant host cell include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142; and 6,177,611.

In choosing a promoter to use in the methods of the disclosure, it may be desirable to use a tissue-specific or developmentally regulated promoter.

A tissue-specific or developmentally-regulated promoter is a DNA sequence which regulates the expression of a DNA sequence selectively in the cells/tissues of a plant, such as in those cells/tissues critical to tassel development, seed set, or both, and which usually limits the expression of such a DNA sequence to the developmental period of interest (e.g. tassel development or seed maturation) in the plant. Any identifiable promoter which causes the desired temporal and spatial expression may be used in the methods of the present disclosure.

Many leaf-preferred promoters are known in the art (Yamamoto et al. (1997) *Plant J.* 12(2):255-265; Kwon et al. (1994) *Plant Physiol.* 105:357-367; Yamamoto et al. (1994) *Plant Cell Physiol.* 35(5):773-778; Gotor et al. (1993) *Plant J.* 3:509-518; Orozco et al. (1993) *Plant Mol. Biol.* 23(6):1129-1138; and Matsuoka et al. (1993) *Proc. Natl. Acad. Sci. USA* 90(20):9586-9590).

Promoters which are seed or embryo-specific and may be useful in the disclosure include soybean Kunitz trypsin inhibitor (Kti3, Jofuku and Goldberg. (1989) *Plant Cell* 1:1079-1093), convicilin, vicilin, and legumin (pea cotyledons) (Rerie, W. G., et al. (1991) *Mol. Gen. Genet.* 259:149-157; Newbigin, E. J., et al. (1990) *Planta* 180:461-470; Higgins, T. J. V., et al. (1988) *Plant. Mol. Biol.* 11:683-695), zein (maize endosperm) (Schemthaner, J. P., et al. (1988) *EMBO J.* 7:1249-1255), phaseolin (bean cotyledon) (Segupta-Gopalan, C., et al. (1985) *Proc. Natl. Acad. Sci.* 82:3320-3324), phytohemagglutinin (bean cotyledon) (Voelker, T. et al. (1987) *EMBO J.* 6:3571-3577), B-conglycinin and glycinin (soybean cotyledon) (Chen, Z-L, et al. (1988) *EMBO J.* 7:297-302), glutelin (rice endosperm), hordein (barley endosperm) (Marris, C., et al. (1988) *Plant Mol. Biol.* 10:359-366), glutenin and gliadin (wheat endosperm) (Colot, V., et al. (1987) *EMBO J.* 6:3559-3564). Promoters of seed-specific genes operably linked to heterologous coding regions in chimeric gene constructions maintain their temporal and spatial expression pattern in transgenic plants. Such examples include *Arabidopsis* 2S seed storage protein gene promoter to express enkephalin peptides in *Arabidopsis* and *Brassica napus* seeds (Vanderkerckhove et al. (1989) *Bio/Technology* 7:L929-932), bean lectin and bean beta-phaseolin promoters to express luciferase (Riggs et al. (1989) *Plant Sci.* 63:47-57), and wheat glutenin promoters to express chloramphenicol acetyl transferase (Colot et al. (1987) *EMBO J* 6:3559-3564).

Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

Promoters for use in certain embodiments include the following: 1) the stress-inducible promoter RD29A (Kasuga et al. (1999) *Nature Biotechnol.* 17:287-291); 2) the stress-inducible promoter Rab17 (Vilardell et al. (1991) *Plant Mol. Bio.* 17:985-993; Kamp Busk et al. (1997) *Plant J*11(6):1285-1295); 3) the barley promoter B22E whose expression is specific to the pedicel in developing maize kernels ("Primary Structure of a Novel Barley Gene Differentially Expressed in Immature Aleurone Layers". Klemsdal, S. S. et al. (1991) *Mol. Gen. Genet.* 228(1/2):9-16); and 4) maize promoter Zag2 ("Identification and molecular characterization of ZAG1, the maize homolog of the *Arabidopsis* floral homeotic gene AGAMOUS", Schmidt, R. J. et al. (1993) *Plant Cell* 5(7):729-737; "Structural characterization, chromosomal localization and phylogenetic evaluation of two pairs of AGAMOUS-like MADS-box genes from maize", Theissen et al. (1995) *Gene* 156(2):155-166; NCBI GenBank Accession No. X80206)). Zag2 transcripts can be detected 5 days prior to pollination to 7 to 8 days after pollination ("DAP"), and directs expression in the carpel of developing female inflorescences and Cim1 which is specific to the nucleus of developing maize kernels. Cim1 transcript is detected 4 to 5 days before pollination to 6 to 8 DAP. Other useful promoters include any promoter which can be derived from a gene whose expression is maternally associated with developing female florets.

For the expression of a polynucleotide in developing seed tissue, promoters of particular interest include seed-preferred promoters, particularly early kernel/embryo promoters and late kernel/embryo promoters. Kernel development post-pollination is divided into approximately three primary phases. The lag phase of kernel growth occurs from about 0 to 10-12 DAP. During this phase the kernel is not growing significantly in mass, but rather important events are being carried out that will determine kernel vitality (e.g., number of cells established). The linear grain fill stage begins at about 10-12 DAP and continues to about 40 DAP. During this stage of kernel development, the kernel attains almost all of its final mass, and various storage products (i.e., starch, protein, oil) are produced. Finally, the maturation phase occurs from about 40 DAP to harvest. During this phase of kernel development the kernel becomes quiescent and begins to dry down in preparation for a long period of dormancy prior to germination. As defined herein "early kernel/embryo promoters" are promoters that drive expression principally in developing seed during the lag phase of development (i.e., from about 0 to about 12 DAP). "Late kernel/embryo promoters", as defined herein, drive expression principally in developing seed from about 12 DAP through maturation. There may be some overlap in the window of expression. The choice of the promoter will depend on the ABA-associated sequence utilized and the phenotype desired.

Early kernel/embryo promoters include, for example, Cim1 that is active 5 DAP in particular tissues (WO 00/11177), which is herein incorporated by reference. Other early kernel/embryo promoters include the seed-preferred promoters end1 which is active 7-10 DAP, and end2, which is active 9-14 DAP in the whole kernel and active 10 DAP in the endosperm and pericarp (WO 00/12733), herein incorporated by reference. Additional early kernel/embryo promoters that find use in certain methods of the present disclosure include the seed-preferred promoter ltp2 (U.S. Pat. No. 5,525,716); maize Zm40 promoter (U.S. Pat. No. 6,403,862); maize nuc1c (U.S. Pat. No. 6,407,315); maize ckx1-2 promoter (U.S. Pat. No. 6,921,815 and US Patent Application Publication Number 2006/0037103); maize lec1 promoter (U.S. Pat. No. 7,122,658); maize ESR promoter (U.S. Pat. No. 7,276,596); maize ZAP promoter (U.S. Patent Application Publication Numbers 20040025206 and 20070136891); maize promoter eep1 (U.S. Patent Application Publication Number 20070169226); and maize promoter ADF4 (U.S. Patent Application No. 60/963,878, filed 7 Aug. 2007).

Additional promoters for regulating the expression of the nucleotide sequences of the present disclosure in plants are stalk-specific promoters, including the alfalfa S2A promoter (GenBank Accession No. EF030816; Abrahams et al. (1995) *Plant Mol. Biol.* 27:513-528) and S2B promoter (GenBank Accession No. EF030817) and the like, herein incorporated by reference.

Promoters may be derived in their entirety from a native gene, or be composed of different elements derived from different promoters found in nature, or even comprise synthetic DNA segments.

Promoters for use in certain embodiments of the current disclosure may include: RIP2, mLIP15, ZmCOR1, Rab17, CaMV 35S, RD29A, B22E, Zag2, SAM synthetase, ubiquitin, CaMV 19S, nos, Adh, sucrose synthase, R-allele, the vascular tissue preferred promoters S2A (Genbank accession number EF030816) and S2B (Genbank accession number EF030817), and the constitutive promoter GOS2 from *Zea mays*; root preferred promoters, such as the maize NAS2 promoter, the maize Cyclo promoter (US 2006/0156439, published Jul. 13, 2006; U.S. Pat. No. 7,268,226, issued Sep. 11, 2007), the maize ROOTMET2 promoter (WO05063998, published Jul. 14, 2005; U.S. Pat. No. 7,214,855, issued May 8, 2007), the CR1BIO promoter (WO06055487, published May 26, 2006; U.S. Pat. No. 7,268,270 issued Sep. 11, 2007; U.S. Pat. No. 7,456,334, issued Nov. 25, 2008), the CRWAQ81 promoter (WO05035770, published Apr. 21, 2005; U.S. Pat. No. 7,411,112 issued Aug. 12, 2008) and the maize ZRP2.47 promoter (NCBI accession number: U38790; GI No. 1063664).

Recombinant DNA constructs of the present disclosure may also include other regulatory sequences, including but not limited to, translation leader sequences, introns, and polyadenylation recognition sequences. In certain embodiments, a recombinant DNA construct further comprises an enhancer or silencer.

An intron sequence can be added to the 5' untranslated region, the protein-coding region or the 3' untranslated region to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg. (1988) *Mol. Cell Biol.* 8:4395-4405; Callis et al. (1987) *Genes Dev.* 1:1183-1200).

Any plant can be selected for the identification of regulatory sequences and DN-DTP1 polypeptide genes to be used in recombinant DNA constructs of the present disclosure. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, *eucalyptus*, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, ornamental plant, palm, *papaya*, parsley, parsnip, pea, peach, peanut, pear, pepper, persimmon, pine, pineapple, plantain, plum, pomegranate, poplar, potato, pumpkin, quince, *radiata* pine, radicchio, radish, rapeseed, raspberry, rice, rye, sorghum, Southern pine, soybean, spinach, squash, strawberry, sugarbeet, sugarcane, sunflower, sweet potato, sweetgum, switchgrass, tangerine, tea, tobacco, tomato, triticale, turf, turnip, vine, watermelon, wheat, yams, and zucchini.

Compositions:

A composition of the present disclosure is a plant comprising in its genome any of the recombinant DNA constructs of the present disclosure (such as any of the constructs discussed above). Compositions also include any progeny of the plant, and any seed obtained from the plant or its progeny, wherein the progeny or seed comprises within its genome the recombinant DNA construct. Progeny includes subsequent generations obtained by self-pollination or out-crossing of a plant. Progeny also includes hybrids and inbreds.

In hybrid seed propagated crops, mature transgenic plants can be self-pollinated to produce a homozygous inbred plant. The inbred plant produces seed containing the newly introduced recombinant DNA construct. These seeds can be grown to produce plants that would exhibit an altered agronomic characteristics (e.g., an increased agronomic characteristics optionally under water limiting conditions), or used in a breeding program to produce hybrid seed, which can be grown to produce plants that would exhibit such an altered agronomic characteristics. The seeds may be maize seeds or rice seeds.

The plant may be a monocotyledonous or dicotyledonous plant, for example, a rice or maize or soybean plant, such as a maize hybrid plant or a maize inbred plant. The plant may also be sunflower, sorghum, canola, wheat, alfalfa, cotton, barley, millet, sugar cane or switchgrass.

The recombinant DNA construct may be stably integrated into the genome of the plant.

Particular embodiments include but are not limited to the following:

1. A transgenic plant (for example, a rice or maize or soybean plant) comprising in its genome a recombinant DNA construct comprising a polynucleotide operably linked to at least one regulatory sequence, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74.%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4, and wherein said plant exhibits increased drought tolerance and/or paraquat tolerance when compared to a control plant. The plant may further exhibit an alteration of at least one agronomic characteristics when compared to the control plant.

2. A transgenic plant (for example, a rice or maize or soybean plant) comprising in its genome a recombinant DNA construct comprising a polynucleotide operably linked to at least one regulatory sequence, wherein said polynucleotide encodes a DN-DTP1 polypeptide, and wherein said plant exhibits increased drought tolerance when compared to a control plant. The plant may further exhibit an alteration of at least one agronomic characteristic when compared to the control plant.

3. A transgenic plant (for example, a rice or maize or soybean plant) comprising in its genome a recombinant DNA construct comprising a polynucleotide operably linked to at least one regulatory sequence, wherein said polynucleotide encodes a DN-DTP1 polypeptide, and wherein said plant exhibits an alteration of at least one agronomic characteristics when compared to a control plant.

4. A transgenic plant (for example, a rice or maize or soybean plant) comprising in its genome a recombinant DNA construct comprising a polynucleotide operably linked to at least one regulatory element, wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4, and wherein said plant exhibits an alteration of at least one agronomic characteristics when compared to a control plant.

5. Any progeny of the above plants in embodiments 1-4, any seeds of the above plants in embodiments 1-4, any seeds of progeny of the above plants in embodiments 1-4, and cells from any of the above plants in embodiments 1-4 and progeny thereof.

In any of the foregoing embodiments 1-5 or other embodiments, the DN-DTP1 polypeptide may be from *Oryza sativa, Arabidopsis thaliana, Zea mays, Glycine max, Glycine tabacina, Glycine soja* or *Glycine tomentella*.

In any of the foregoing embodiments 1-5 or other embodiments, the recombinant DNA construct may comprise at least a promoter functional in a plant as a regulatory sequence.

In any of the foregoing embodiments 1-5 or other embodiments, the alteration of at least one agronomic characteristics is either an increase or decrease.

In any of the foregoing embodiments 1-5 or other embodiments, the at least one agronomic characteristics may be selected from the group consisting of greenness, grain yield, growth rate, biomass, fresh weight at maturation, dry weight at maturation, fruit yield, grain yield, total plant nitrogen content, fruit nitrogen content, seed nitrogen content, nitrogen content in a vegetative tissue, total plant free amino acid content, fruit free amino acid content, seed free amino acid content, free amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, salt tolerance, tiller number, panicle size, early seedling vigor and seedling emergence under low temperature stress. For example, the alteration of at least one agronomic characteristic may be an increase in grain yield, greenness or biomass.

In any of the foregoing embodiments 1-5 or other embodiments, the plant may exhibit the alteration of at least one agronomic characteristics when compared, under water limiting conditions, to a control plant.

In any of the foregoing embodiment 1-5 or other embodiments, the plant may exhibit the alteration of at least one agronomic characteristic when compared, under oxidative stress (e.g. paraquat) conditions, to a control plant.

"Drought" refers to a decrease in water availability to a plant that, especially when prolonged or when occurring during critical growth periods, can cause damage to the plant or prevent its successful growth (e.g., limiting plant growth or grain yield).

"Drought tolerance" reflects a plant's ability to survive under drought without exhibiting substantial physiological or physical deterioration, and/or its ability to recover when water is restored following a period of drought.

"Drought tolerance activity" of a polypeptide indicates that overexpression of the polypeptide in a transgenic plant confers increased drought tolerance of the transgenic plant relative to a reference or control plant.

"Increased drought tolerance" of a plant is measured relative to a reference or control plant, and reflects ability of the plant to survive under drought conditions with less physiological or physical deterioration than a reference or control plant grown under similar drought conditions, or ability of the plant to recover more substantially and/or more quickly than would a control plant when water is restored following a period of drought.

"Paraquat" (1,1-dimethyl-4,4-bipyridinium dichloride), is a foliar-applied and non-selective bipyridinium herbicides, and causes photooxidative stress which further cause damage to plant or prevent its successful growth.

"Paraquat tolerance" is a trait of a plant, reflects improved ability to survive and/or grow when treated with Paraquat solution, compared to a reference or control plant.

"Increased paraquat tolerance" of a plant is measured relative to a reference or control plant, and reflects ability of the plant to survive with less physiological or physical deterioration than a reference or control plant after treated with paraquat solution. In general, tolerance to relative low level of paraquat can be used as a marker of abiotic stress tolerance, such as drought tolerance.

"Oxidative stress" reflects an imbalance between the systemic manifestation of reactive oxygen species and a biological system's ability to readily detoxify the reactive intermediates or to repair the resulting damage. Disturbances in the normal redox state of cells can cause toxic effects through the production of peroxides and free radicals that damage all components of the cell, including proteins, lipids, and DNA. http://en.wikipedia.org/wiki/Oxidative_stress.

The examples below describe some representative protocols and techniques for simulating drought conditions and/or evaluating drought tolerance.

One can also evaluate drought tolerance by the ability of a plant to maintain sufficient yield (at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% yield) in field testing under simulated or naturally-occurring drought conditions (e.g., by measuring for substantially equivalent yield under drought conditions compared to non-drought conditions, or by measuring for less yield loss under drought conditions compared to yield loss exhibited by a control or reference plant).

Parameters such as recovery degree, survival rate, paraquat tolerance rate, gene expression level, water use efficiency, level or activity of an encoded protein, and others are typically presented with reference to a control cell or control plant. A "control" or "control plant" or "control plant cell" provides a reference point for measuring changes in phenotype of a subject plant or plant cell in which genetic alteration, such as transformation, has been effected as to a gene of interest. A subject plant or plant cell may be descended from a plant or cell so altered and will comprise the alteration. One of ordinary skill in the art would readily recognize a suitable control or reference plant to be utilized when assessing or measuring an agronomic characteristics or phenotype of a transgenic plant using compositions or methods as described herein. For example, by way of non-limiting illustrations:

1. Progeny of a transformed plant which is hemizygous with respect to a recombinant DNA construct, such that the progeny are segregating into plants either comprising or not comprising the recombinant DNA construct: the progeny comprising the recombinant DNA construct would be typically measured relative to the progeny not comprising the recombinant DNA construct. The progeny not comprising the recombinant DNA construct is the control or reference plant.

2. Introgression of a recombinant DNA construct into an inbred line, such as in rice and maize, or into a variety, such as in soybean: the introgressed line would typically be measured relative to the parent inbred or variety line (i.e., the parent inbred or variety line is the control or reference plant).

3. Two hybrid lines, wherein the first hybrid line is produced from two parent inbred lines, and the second hybrid line is produced from the same two parent inbred lines except that one of the parent inbred lines contains a recombinant DNA construct: the second hybrid line would typically be measured relative to the first hybrid line (i.e., the first hybrid line is the control or reference plant).

4. A transgenic plant comprising a recombinant DNA construct: the plant may be assessed or measured relative to a control plant not comprising the recombinant DNA construct but otherwise having a comparable genetic background to the plant (e.g., sharing at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity of nuclear genetic material compared to the plant comprising the recombinant DNA construct). There are many laboratory-based techniques available for the analysis, comparison and characterization of plant genetic backgrounds; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLP®s), and Simple Sequence Repeats (SSRs) which are also referred to as Microsatellites.

A control plant or plant cell may comprise, for example: (a) a wild-type (WT) plant or cell, i.e., of the same genotype as the starting material for the genetic alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimulus that would induce expression of the gene of interest or (e) the subject plant or plant cell itself, under conditions in which the gene of interest is not expressed. A control may comprise numerous individuals representing one or more of the categories above; for example, a collection of the non-transformed segregants of category "c" is often referred to as a bulk null.

Methods:

Methods include but are not limited to methods for increasing drought tolerance in a plant, methods for evaluating drought tolerance in a plant, methods for increasing paraquat tolerance, methods for altering an agronomic characteristics in a plant, methods for determining an alteration of an agronomic characteristics in a plant, and methods for producing seed. The plant may be a monocotyledonous or dicotyledonous plant, for example, a rice, maize or soybean plant. The plant may also be sunflower, canola, wheat, alfalfa, cotton, rice, barley, millet, sugar cane or sorghum. The seed may be a maize or soybean seed, for example, a maize hybrid seed or maize inbred seed.

Methods include but are not limited to the following:

A method for transforming a cell comprising transforming a cell with any one or more of the isolated polynucleotides of the present disclosure, wherein, in particular embodiments, the cell is eukaryotic cell, e.g., a yeast, insect or plant cell; or prokaryotic cell, e.g., a bacterial cell.

A method for producing a transgenic plant comprising transforming a plant cell with any of the isolated polynucleotides or recombinant DNA constructs of the present disclosure and regenerating a transgenic plant from the transformed plant cell, wherein, the transgenic plant and the transgenic seed obtained by this method may be used in other methods of the present disclosure.

A method for isolating a polypeptide of the disclosure from a cell or culture medium of the cell, wherein the cell comprises a recombinant DNA construct comprising a polynucleotide of the disclosure operably linked to at least one regulatory sequence, and wherein the transformed host cell is grown under conditions that are suitable for expression of the recombinant DNA construct.

A method for altering the expression level of a polypeptide of the disclosure in a host cell comprising: (a) transforming a host cell with a recombinant DNA construct of the present disclosure; and (b) growing the transformed host cell under conditions that are suitable for the expression of the recombinant DNA construct, wherein the expression of the recombinant DNA construct results in production of altered levels of the polypeptide of the disclosure in the transformed host cell.

A method of increasing drought tolerance and/or paraquat tolerance in a plant, comprising: (a) introducing into a regenerable plant cell a recombinant DNA construct comprising a polynucleotide operably linked to at least one regulatory sequence (for example, a promoter functional in a plant), wherein the polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4; (b) regenerating a transgenic plant from the regenerable plant cell after step (a), wherein the transgenic plant comprises in its genome the recombinant DNA construct and exhibits increased drought tolerance and/or paraquat tolerance when compared to a control plant; and further (c) obtaining a progeny plant derived from the transgenic plant, wherein said progeny plant comprises in its genome the recombinant DNA construct and exhibits increased drought tolerance and/or paraquat tolerance when compared to a control plant.

A method of evaluating drought tolerance and/or paraquat tolerance in a plant comprising (a) obtaining a transgenic plant, which comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, to SEQ ID NO: 4; (b) obtaining a progeny plant derived from said transgenic plant, wherein the progeny plant comprises in its genome the recombinant DNA construct; and (c) evaluating the progeny plant for drought tolerance and/or paraquat tolerance compared to a control plant.

A method of determining an alteration of an agronomic characteristics in a plant comprising (a) obtaining a transgenic plant which comprises in its genome a recombinant DNA construct comprising a polynucleotide operably linked to at least one regulatory sequence (for example, a promoter functional in a plant), wherein said polynucleotide encodes a polypeptide having an amino acid sequence of at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% sequence identity, based on the Clustal V method of alignment, when compared to SEQ ID NO: 4; (b) obtaining a progeny plant derived from said transgenic plant, wherein the progeny plant comprises in its genome the recombinant DNA construct; and (c) determining whether the progeny plant exhibits an alteration in at least one agronomic characteristics when compared, optionally under water limiting conditions, to a control plant.

A method of producing seed (for example, seed that can be sold as a drought tolerant product offering) comprising any of the preceding methods, and further comprising obtaining seeds from said progeny plant, wherein said seeds comprise in their genome said recombinant DNA construct.

In any of the preceding methods or any other embodiments of methods of the present disclosure, in said introducing step, the said regenerable plant cell may comprise a callus cell, an embryogenic callus cell, a gametic cell, a meristematic cell, or a cell of an immature embryo. The regenerable plant cells may derive from an inbred maize plant.

In any of the preceding methods or any other embodiments of methods of the present disclosure, said regenerating step may comprise the following: (i) culturing said transformed plant cells in a medium comprising an embryogenic promoting hormone until callus organization is observed; (ii) transferring said transformed plant cells of step (i) to a first media which includes a tissue organization promoting hormone; and (iii) subculturing said transformed plant cells after step (ii) onto a second media, to allow for shoot elongation, root development or both.

In any of the preceding methods or any other embodiments of methods of the present disclosure, the at least one agronomic characteristics may be selected from the group consisting of greenness, grain yield, growth rate, biomass, fresh weight at maturation, dry weight at maturation, fruit yield, grain yield, total plant nitrogen content, fruit nitrogen content, seed nitrogen content, nitrogen content in a vegetative tissue, total plant free amino acid content, fruit free amino acid content, seed free amino acid content, amino acid content in a vegetative tissue, total plant protein content, fruit protein content, seed protein content, protein content in a vegetative tissue, drought tolerance, nitrogen uptake, root lodging, harvest index, stalk lodging, plant height, ear height, ear length, tiller number, panicle size, salt tolerance, early seedling vigor and seedling emergence under low temperature stress. The alteration of at least one agronomic characteristic may be an increase in grain yield, greenness or biomass.

In any of the preceding methods or any other embodiments of methods of the present disclosure, the plant may exhibit the alteration of at least one agronomic characteristics when compared, under water limiting conditions, to a control plant.

In any of the preceding methods or any other embodiments of methods of the present disclosure, alternatives exist for introducing into a regenerable plant cell a recombinant DNA construct comprising a polynucleotide operably linked to at least one regulatory sequence. For example, one may introduce into a regenerable plant cell a regulatory sequence (such as one or more enhancers, optionally as part of a transposable element), and then screen for an event in which the regulatory sequence is operably linked to an endogenous gene encoding a polypeptide of the instant disclosure.

The introduction of recombinant DNA constructs of the present disclosure into plants may be carried out by any suitable technique, including but not limited to direct DNA uptake, chemical treatment, electroporation, microinjection, cell fusion, infection, vector-mediated DNA transfer, bombardment, or *Agrobacterium*-mediated transformation. Techniques for plant transformation and regeneration have been described in International Patent Publication WO 2009/006276, the contents of which are herein incorporated by reference.

In addition, methods to modify or alter the host endogenous genomic DNA are available. This includes altering the host native DNA sequence or a pre-existing transgenic sequence including regulatory elements, coding and non-coding sequences. These methods are also useful in targeting nucleic acids to pre-engineered target recognition sequences in the genome. As an example, the genetically modified cell or plant described herein, is generated using "custom" meganucleases produced to modify plant genomes (e.g., WO 2009/114321; Gao et al. (2010) Plant Journal 1:176-187). Another site-directed engineering is through the use of zinc finger domain recognition coupled with the restriction properties of restriction enzyme (e.g., Urnov, et al. (2010) *Nat Rev Genet.* 11(9):636-46; Shukla, et al. (2009) *Nature* 459 (7245):437-41).

The development or regeneration of plants containing the foreign, exogenous isolated nucleic acid fragment that encodes a protein of interest is well known in the art. The regenerated plants may be self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant containing a desired polypeptide is cultivated using methods well known to one skilled in the art.

The skilled artisan will further appreciate that changes can be introduced by mutation of the nucleic acid sequences, thereby leading to changes in either the expression of encoded mRNAs or the amino acid sequence of the encoded polypeptide, resulting in alteration of the biological activity of the mRNA or protein, respectively, or both. See for example methods described in U.S. patent application Ser. No. 14/463,687 filed on Aug. 20, 2014, incorporated by reference in its entirety herein. Thus, variant nucleic acid molecules can be created by introducing one or more nucleotide substitutions, additions and/or deletions into the corresponding nucleic acid sequence or surrounding sequences disclosed herein. Such variant nucleic acid sequences are also encompassed by the present disclosure.

Variant nucleic acid sequences can be made by introducing sequence changes randomly along all or part of the genic region, including, but not limited to, chemical or irradiation mutagenesis and oligonucleotide-mediated mutagenesis (OMM) (Beetham et al. 1999; Okuzaki and Toriyama 2004). Alternatively or additionally, sequence changes can be introduced at specific selected sites using double-strand-break technologies such as ZNFs, custom designed homing endonucleases, TALENs, CRISPR/CAS (also referred to as guide RNA/Cas endonuclease systems (U.S. patent application Ser. No. 14/463,687 filed on Aug. 20, 2014), or other protein and/or nucleic acid based mutagenesis technologies. The resultant variants can be screened for altered activity. It will be appreciated that the techniques are often not mutually exclusive. Indeed, the various methods can be used singly or in combination, in parallel or in series, to create or access diverse sequence variants.

EXAMPLES

Certain embodiments of the present disclosure are further illustrated in the following examples, in which parts and percentages are by weight and degrees are Celsius, unless otherwise stated. It should be understood that these examples, while indicating embodiments of the disclosure, are given by way of illustration only. From the above discussion and these examples, one skilled in the art can ascertain the essential characteristics of this disclosure, and without departing from the spirit and scope thereof, can make various changes and modifications of the disclosure to adapt it to various usages and conditions. Thus, various modifications of the disclosure in addition to those shown and described herein will be apparent to those skilled in the art from the foregoing description. Such modifications are also intended to fall within the scope of the appended claims.

Example 1

Creation of a Rice Population with an Activation-Tagging Construct

In this research, a 4×CaMV 35S enhancer-based binary construct was used, and the rice activation tagging population was developed from Zhonghua11 (*Oryza sativa* L. Zhonghua11) which was transformed by Agrobacteria-mediated transformation. Zhonghua11 was cultivated by institute of crop sciences, Chinese Academy of Agricultural Sciences. The first batch of seeds used in this research was provided by Beijing Weiming Kaituo Agriculture Biotech Co., Ltd. Calli induced from embryos was transformed with Agrobacteria with the vector. The transgenic events generated were developed and the transgenic seeds were harvested to form the rice activation tagging population.

Example 2

Seedling Screens to Identify Lines with Enhanced Drought Tolerance Under Greenhouse Conditions Seedling screens for drought tolerance were carried out in greenhouse. Two types of lamps are provided as light source, i.e. sodium lamp and metal halide lamp, the ratio is 1:1. Lamps provide the 16 h/8 h period of day/night, and are placed approximately 1.5 m above the seedbed. The light intensity 30 cm above the seedbed is measured as 10,000-20,000 lx in sunny day, while 6,000-10,000 lx in cloudy day, the relative humidity ranges from 30% to 90%, and the temperature ranges from 20 to 35° C.

In the first round screen, $T_1$ seeds were used. Fourteen uniform seedlings from mutant rice lines, and 16 ZH11-TC seedlings (Zhonghua11 generated from tissue culture procedure) were used for the drought tolerance screens. The seedlings were planted in one tray filled with mixture of planting soil (FangJie soil from Beijing HuiYeShengDa Center), vermiculite (Beijing QingYuanShiJi Garden Center) and sand (Beijing Shuntun Construction Material Market) (V:V:V=3:3:2). After all the seedlings grew to 3-leaf stage, watering was stopped and the trays were kept in a dry place until the leaves became curved (approximately 9-15 days depending on the seasons). The trays were transferred into water pool and the seedlings recovered for 5-7 days, and then the recovery degrees of plants were scored. The following scoring system was used: one green stem=1, one green leaf=1, a half green stem or leaf=0.5, one third green leaf=0.2, no green leaf or stem=0. The recovery degree is the sum of the score of the green tissues, and the data were statistically analyzed using SAS-software. The lines which showed significant difference from controls were considered as primary positive lines.

$T_2$ seeds were used in the following test. 20 or 60 plants were screened, and were analyzed only with respect to the plants generated from Zhonghua11 by tissue culture procedure, using SAS software (P<0.05).

Survival rate was also used as a parameter for the screens, which is the percentage of survived plants over the total plant number.

Lines which passed the above screens were planted in greenhouse soil or in field (depending the seasons) for harvesting leaf materials and molecular cloning of the T-DNA-flanking sequences and candidate genes. In general, 20-30 g of fresh leaf tissues were harvested from 30 uniform seedlings of the same line, frozen in liquid nitrogen, and stored in −80° C. freezer.

Example 3

Results for Line AH00838

In repeated greenhouse drought screening assays, line AH00838 consistently showed enhanced drought tolerance compared to the ZH11-TC (Zhonghua11 generated from tissue culture procedure).

As shown in Table 2, 9 of 14 $T_1$ plants (64.3%) from line AH00838 were recovered or survived under greenhouse drought stress conditions; while only 31.2% ZH11-TC plants survived. The result indicates that AH00838 has significantly enhanced drought tolerance compared to ZH11-TC.

Observations were further carried out at $T_2$ generation. Three rounds of screens were carried out. In the first round screen, 70% of AH00838 plants survived, while only 19% ZH11-TC survived. The survival rate and the average recovery degree of AH00838 rice plants were significantly better than those of ZH11-TC, even though the drought stresses were increased during the following two rounds of screens (Table 3). These results further demonstrate that AH00838 has enhanced drought tolerance under greenhouse drought conditions at seedling stages.

TABLE 2

Drought tolerance assay of AH00838 plants at $T_1$ generation under greenhouse conditions

| Line | Survival rate (%) | Average recovery degree | P value | P ≤ 0.05 |
|---|---|---|---|---|
| AH00838 | 64.3 | 0.64 | 0.003 | Y |
| ZH11-TC | 31.2 | 0.28 | | |

TABLE 3

Drought tolerance assay of AH00838 rice plants at $T_2$ generation under greenhouse conditions

| Line | Screen round | Survival rate (%) | Average recovery degree | P value | P ≤ 0.05 |
|---|---|---|---|---|---|
| AH00838 | 1st | 70.0 | 0.99 | 0.000 | Y |
| ZH11-TC | | 18.8 | 0.26 | | |
| AH00838 | 2nd | 40.0 | 0.73 | 0.002 | Y |
| ZH11-TC | | 13.3 | 0.25 | | |
| AH00838 | 3rd | 13.3 | 0.13 | 0.048 | Y |
| ZH11-TC | | 3.3 | 0.03 | | |

In light of these results, further work was carried out to identify the gene(s) which contributes to the enhanced drought tolerance in AH00838 plants.

Example 4

Identification of Activation-Tagged Genes

Genes flanking the T-DNA insertion locus in the drought-tolerant line AH00838 were identified using one or both of the following two standard procedures: (1) Plasmid Rescue (Friedrich J. Behringer and June I. Medford. (1992), *Plant Molecular Biology Reporter* Vol. 10, 2:190-198); and (2) Inverse PCR (M. J. McPherson and Philip Quirke. (1991), *PCR: a practical approach*, 137-146). For lines with complex multimerized T-DNA inserts, plasmid rescue and inverse PCR may both prove insufficient to identify candidate genes. In these cases, other procedures, including TAIL PCR (Liu et al. (1995), *Plant J.* 8:457-463) can be employed.

A successful sequencing result is one where a single DNA fragment contains a T-DNA border sequence and flanking genomic sequence. When a tag of genomic sequence flanking a T-DNA insert is obtained, candidate genes are identified by alignment to publicly available rice genome sequence. Specifically, the annotated genes nearest the enhancer elements/T-DNA RB and LB are candidates of genes that are activated.

To verify that an identified gene is near a T-DNA and to rule out the possibility that the DNA fragment is a chimeric cloning artifact, a diagnostic PCR on genomic DNA is done with one oligo in the T-DNA and one oligo specific for the local genomic DNA. Genomic DNA samples that give a PCR product are interpreted as representing a T-DNA insertion. This analysis also verifies a situation in which more than one insertion event occurs in the same line, e.g., if multiple differing genomic fragments are identified in Plasmid Rescue and/or Inverse-PCR analyses.

Genomic DNA was isolated from leaf tissues of the AH00838 line using CTAB method (Murray, M. G. and W. F. Thompson. (1980) *Nucleic Acids Res.* 8: 4321-4326).

10 μg of genomic DNA from AH00838 was digested by 2 μL restriction enzyme BglII (NEB). After self-ligation and transformation into competent *E. coli* DH5a through electroporation, the survived colonies on an ampicillin-containing plate were validated by colony-PCR using primers of P2up 5389 and P2down 3534.

P2up 5389:
(SEQ ID NO: 5)
5'-ACCCCAGGCTTTACACTTTATGCTTCC-3'

P2down 3534:
(SEQ ID NO: 6)
5'-AACCCACTCGTGCACCCAACTGATC-3'

PCR Reaction Mixture and Procedure:

| Reaction mix | (25 μL) |
|---|---|
| Template | 2 μL |
| Primer (10 μM) | each 1 μL |
| dNTPs (2.5 mM each) | 2 μL |
| La Taq (TaKaRa) | 0.2 μL |
| 10 × LA PCR buffer II | 1.25 μL |
| 2 × GC bufferI | 6.25 μL |
| ddH$_2$O | 11.3 μL |

PCR Cycle:

| 94° C. | 3 min | |
| 98° C. | 20 s | } 30 Cycles |
| 68° C. | 15 min | |
| 72° C. | 10 min | |

All survived colonies on ampicillin-containing plate were analyzed and all of them produced a band about 4 kb in size on an agarose gel electrophoresis. After sequencing the 4 kb DNA fragment, the flanking sequence of T-DNA in AH00838 was obtained. This nucleotide sequence was shown as SEQ ID NO: 1.

T-DNA inserted in Chromosome 4 of AH00838's genome, and there is only one T-DNA insertion locus in the rice genome of AH00838.

OsDN-DTP1 gene is near the T-DNA insertion locus, and AH00838 line had enhanced drought tolerance, so this gene was cloned and validated as to its functions in drought tolerance and other agronomic trait improvement.

Example 5

OsDN-DTP1 Gene Cloning and Vector Construction

The OsDN-DTP1 (Os04g0208800) gene was amplified by using KOD-FX PCR mix (TOYOBO), using cDNA of Zhonghua11 rice as PCR template. The primers are:

```
45-Os04g0208800-F:
                                      (SEQ ID NO: 7)
5'-AAAGGATCCTACATTATTACATATGTTCCGTTC-3'

45-Os04g0208800-R:
                                      (SEQ ID NO: 8)
5'-GGCGTTGCTGGTGCCGTTCAG-3'
```

A BamHI site which was underlined was designed in primer 45-Os04g0208800-F. An expected 400 bp DNA fragment was amplified, purified, digested by BamHI, and ligated with an overexpression vector DP0005 which was digested by BglII and NruI. The right clone (DP0006) was confirmed by restriction mapping and DNA sequencing. The nucleotide sequences of OsDN-DTP1 cDNA and CDS, and its encoded protein are shown in SEQ ID NO: 2, SEQ ID NO: 3 and SEQ ID NO: 4, respectively.

Example 6

Vector Construction of DP0005 and DP0009

DP0005 was constructed from pCAMBIA1300 (Cambia, Brisbane, Australia). The CaMV 35S promoter was amplified using template of pCAMBIA1300 and primers of 35sF and 35sR. The restriction enzyme sites HindIII and PstI were added at 35S CaMV promoter 5'- and 3'-ends, respectively.

```
35sF:
                                      (SEQ ID NO: 9)
5'- AAGCTTAGAGCAGCTTGGCAACATGGTGGAGCAC-3'

35sR:
                                      (SEQ ID NO: 10)
5'-CTGCAGAGAGATAGATTTGTAGAGAGAG-3'
```

This amplified CaMV35S promoter fragment was digested by HindIII and PstI and ligated into HindIII-PstI-digested pCAMBIA1300 to produce pCAMBIA1300-35s. The Terminator NOS polyA was amplified using template of pCAMBIA1303 and primers of TnosF and TnosR. The restriction enzyme sites PstI+BglII+KpnI+NcoI+salI and BamHI were designed in Terminator NOS polyA 5' and 3' ends of the primers, respectively.

```
TnosF:
                                      (SEQ ID NO: 11)
5'-CTGCAGAGATCTGGTACCGGTCGCCACCATGGAAGTCGACGTTTCTT
GTTTCTTAAGATTGAATCCTGTTG-3'

TnosR:
                                      (SEQ ID NO: 12)
5'- GGATCCTCTAGTCCCGATCTAGTAACATAG-3'
```

Terminator NOS polyA fragment was digested with PstI and BamHI and ligated into the PstI-BamHI-digested vector. The produced vector was designed as pCAMBIA1300-35s-Tnos.

The AsRED gene was used from pAsRED2 (Clontech Laboratories Inc.), and inserted in the pCAMBIA1300-35s-Tnos vector to produce pCAMBIA1300-35s-AsRED-Tnos. For convenient construction of gene expression vectors, the new Terminator NOS polyA fragment with BamHI+NruI+SalI site in 5' end and EcoRI in 3' end. The primers are:

```
TnosF2:
                                      (SEQ ID NO: 13)
5'-CCGGGATCCTCGCGAGTCGACCTCCAAGCTGGGCCACAACTGAAG-3'

TnosR2:
                                      (SEQ ID NO: 14)
5'-CGAGAATTCTCTAGTCCCGATCTAGTAACATAG-3'
```

The new Terminator NOS polyA fragment was amplified by PCR using pCAMBIA1300-35s-AsRED-Tnos as a template. This DNA fragment was digested by BamHI and EcoRI, and ligated to pCAMBIA1300-35s-AsRED-Tnos which was digested by BamHI and EcoRI to produce DP0005, an overexpression vector backbone for OsDN-DTP1. DP0005 was digested by BglII and BamHI, and then self-ligated for eliminating the AsRED gene from DP0005 to produce DP0009.

Example 7

OsDN-DTP1 Transgenic Rice Events

Both empty vector (DP0005, VC) and overexpression vector (DP0006) were transformed separately into Zhonghua11 by Agrobacteria-mediated transformation method.

The drought tolerance assay was carried out at $T_2$ generations. Seedlings were cultured to a length of about 1-2 cm in 75 mg/L hygromycin solution for 3-5 days. Only the survived plants (hygromycin-resistant) were used in field drought assays.

The expression levels of OsDN-DTP1 transgene in transgenic DP0006 rice plants were measured by real-time PCR analyses. Leaf samples were collected from different DP0006 rice plants, and a real-time PCR procedure, such as the QuantiTect® Reverse Transcription Kit from Qiagen® and Real Time-PCR (SYBRRPremix Ex Taq™, TaKaRa), is used. EF-1 gene is used as a control to show that the amplification and loading of samples from the tagging line and VC are similar. Assay conditions are optimized for each gene.

The total RNA was extracted from about 50 mg leaf tissues of DP0006 plants at 4-leaf-stage using RNAiso Plus kit (TaKaRa) according to manufacturer's instruction. The cDNA were prepared by RevertAid™ First Strand cDNA Synthesis Kit (Fermentas) and from 500 ng total RNA. The real-time-PCR (SYBRRPremix Ex Taq™, TaKaRa) was conducted using 7,500 Fast real-time PCR equipment and according to the manual (ABI).

The primers for real time PCR for OsDN-DTP1 gene are listed below:

```
DP0006-1:
                                      (SEQ ID NO: 15)
5'-CAACCACAACGCGTATG-3'

DP0006-2:
                                      (SEQ ID NO: 16)
5'-CCTACCAGCTGCAATGC-3'
```

As shown in FIG. 1, OsDN-DTP1 gene overexpressed in DP0006 events, but there is no detectable expression in VC (empty vector DP0005) plants. The expression level in event DP0006.09 is significantly higher than those in other events.

Example 8

Enhanced Drought Tolerance by Overexpression of OsDN-DTP1 Gene

Field drought screens of transformed rice plants were carried out in Hainan Province. For each transgenic event to be tested, 100 positive seeds were soaked in water for 16 h at room temperature, germinated for 36 h at 35-37° C. in an incubator, and planted in a bedded field. At 3-leaf stage, the seedlings were transplanted into the testing field, with 4 replicates and 10 plants per replicate for each transgenic event, and the 4 replicates were planted in the same block. The negative seeds which shown no red color (segregated nulls) under green fluorescent light were planted nearby the transgenic events in the same block, and were used as control in the statistical analysis.

The rice plants were managed as normal practice using pesticides and fertilizers. Watering was stopped at booting stage to generate drought stress at flowering stage depending on the weather (temperature and humidity). In Sanya of Hainan Province, the rice plants were stopped watering 25 days after transplanted in January-February. The rice plants were re-watered one or two times during the drought stress to avoid severe condition and to keep reasonable yield. The soil water content was measured every 3-day at 10 sites per block using TDR300 (Spectrum Technologies, Inc.).

Plant phenotypes were observed and recorded during the experiments. The phenotypes include heading time, leaf rolling, and drought sensitive and tolerant. Special attention was paid to the leaf rolling at noontime. At the end of the season, 24 representative rice plants in the middle of the row per line were harvested and the grain weight per plant was measured.

The grain weight data were statistically analyzed using SAS-ANOVA-mixed model by ASRemI program.

FIG. 2 shows that the soil volumetric moisture content decreased from 28% to 10% during heading and maturation stage, a typical flowering stage drought stress. During maturation stage, it was found that the transgenic event DP0006.04, DP0006.05 and DP0006.15 have significantly better panicle seed setting rate and grain plumpness than that of VC (DP0005-generated event) plants and CK (segregated null) plants after drought stress. The statistical analyses of the yield data indicated that 4 OsDN-DTP1-transgenic events (Table 4) yielded significantly higher than both VC (data not shown) and CK (Table 4). The results indicate that overexpression of OsDN-DTP1 transgene in rice enhanced drought tolerance and panicle seed setting rate and grain plumpness under field drought conditions, and the enhanced drought tolerance is related to the OsDN-DTP1 transgene expression levels.

TABLE 4

Grainyield assay of OsDN-DTP1-rice plants at $T_2$ generation under field drought conditions

| Line | Grain yield per plant (g) | P value | P ≤ 0.05 |
|---|---|---|---|
| DP0006.04 | 11.78 | 0.027 | Y |
| CK | 9.03 | | |
| DP0006.05 | 11.73 | 0.008 | Y |
| CK | 8.44 | | |

TABLE 4-continued

Grainyield assay of OsDN-DTP1-rice plants at $T_2$ generation under field drought conditions

| Line | Grain yield per plant (g) | P value | P ≤ 0.05 |
|---|---|---|---|
| DP0006.14 | 11.12 | 0.010 | Y |
| CK | 8.44 | | |
| DP0006.15 | 12.27 | 0.001 | Y |
| CK | 8.67 | | |

Example 9

Laboratory Paraquat Assays of Transgenic Rice Plants

Paraquat (1,1-dimethyl-4,4-bipyridinium dichloride), is a foliar-applied and non-selective bipyridinium herbicide, and is one of the most widely used herbicides in the world, controlling weeds in a huge variety of crops like corn, rice, soybean etc. In plant cells, paraquat mainly targets to the chloroplasts by accepting electrons from photosystem I and then reacting with oxygen to produce superoxide and hydrogen peroxide, which alters plants' ability to resist photooxidative stress. Drought stress usually leads to increased reactive oxygen species (ROS) in plants and sometimes, the drought tolerance of plant is associated with enhanced antioxidative ability. Paraquat is a potent oxidative stress inducer; it greatly increases the ROS production and inhibits the regeneration of reducing equivalents and compounds necessary for the activity of the antioxidant system. The ROS generation is enhanced under abiotic stress conditions, and the plant responses range from tolerance to death depending on the stress intensity and its associated-ROS levels. Relative low level of paraquat can mimic the stress-associated ROS production and used as a stress tolerance marker in plant stress biology (Hasaneen M. N. A. (2012) Herbicide-Properties, Synthesis and Control of Weeds, Retrieved from http://www.intechopen.com/books/ISBN 978-953-307-803-8). Therefore, the paraquat tolerance of the drought tolerance transgenic rice plants was tested.

Paraquat Assay Methods:

Transgenic rice plants from 9-10 transgenic events of OsDN-DTP1-transgenic rice line were tested by paraquat assay. Tissue-cultured Zhonghua 11 plants (ZH11-TC) were used as controls. $T_2$ transgenic seeds were sterilized and germinated, and cultivated in growth room with the temperature of 28-30° C. and humidity of ~30%. The germinated seeds were placed into a tube with a hole at the bottom, and cultured in water at 30° C. for 5 days till one-leaf and one-terminal bud stage. Uniform seedlings about 3.5-4 cm in height were selected for paraquat testing. Randomized block design was used in this experiment. There were five blocks, each of which has 16×12 holes. Each transgenic event was placed in one row (12 plants/event), and the ZH11-TC controls were placed randomly in 3 rows (3×12 plants) in one block. Then the seedlings were treated with 0.8 μM paraquat solution for 7 days with a 10-h-light/14-h-dark cycle, and the treated seedlings first encountered dark and took up the paraquat solution which was changed every two days. After treated for 7 days, the green seedlings were counted. Those seedlings that maintain green in whole without damage were considered as paraquat tolerant seedlings; while those with bleached leaves or stem were not considered as paraquat tolerant seedling.

Tolerant rate was used as a parameter for this trait screen, which is the percentage of plants which kept green and showed tolerant phenotype over the total plant number.

The data was analyzed at construct level (all transgenic plants compared with the control) and transgenic event level (different transgenic events compared with the control) using a statistic model of "Y~seg+event (seg)+rep+error", random effect of "rep", and statistic method of "SAS Proc Glimmix".

OsDN-DTP1-transgenic rice was tested in paraquat assay for three times.

In the first experiment, after paraquat solution treated for seven days, 387 of 600 OsDN-DTP1-transgenic seedlings (65%) kept green and showed paraquat tolerant phenotype, while 93 of 180 (52%) seedlings from ZH11-TC seedlings showed paraquat tolerant phenotype. The tolerant rate of all screened OsDN-DTP1-transgenic seedlings was significantly greater than that of the ZH11-TC control (P value=0.0015). These results indicate that the OsDN-DTP1-transgenic seedlings exhibited paraquat tolerance enhancement compared with the controls of ZH11-TC at construct level. Further analysis at transgenic event level indicates that 6 of 10 events had significantly greater tolerant rates compared with ZH11-TC control (Table 5). These results demonstrate that OsDN-DTP1-transgenic rice plants had enhanced paraquat tolerance compared with ZH11-TC rice plants at construct and transgenic event level at seedling stages.

Another two experiments were performed to further validate the paraquat tolerance of OsDN-DTP1-transgenic rice. In the second experiment, 284 of 564 OsDN-DTP1-transgenic seedlings (50%) kept green and showed paraquat tolerant phenotype, while 76 of 216 (35%) seedlings from ZH11-TC seedlings showed paraquat tolerant phenotype. The tolerant rate of all screened OsDN-DTP1-transgenic seedlings was significantly greater than that of the ZH11-TC control (P value=0.0003). In the third experiment, 297 of 564 OsDN-DTP1-transgenic seedlings (53%) kept green and showed paraquat tolerant phenotype, while 59 of 216 (27%) seedlings from ZH11-TC seedlings showed paraquat tolerant phenotype. The tolerant rate of all screened OsDN-DTP1-transgenic seedlings was significantly greater than that of the ZH11-TC control (P value=0.0000). And the analysis at transgenic event level of the second experiment is shown in Table 6. These results demonstrate that OsDN-DTP1-transgenic rice plants had enhanced paraquat tolerance compared with ZH11-TC rice plants at construct and transgenic event level at seedling stages. The OsDN-DTP1 gene functions in enhancing paraquat tolerance or antioxidative ability of transgenic plants.

Overexpression of OsDN-DTP1 gene can enhance the field drought tolerance of transgenic plants during the development as illustrated in Example 8; and the cross-validation results in paraquat assay further confirmed that OsDN-DTP1 plays a role in enhancing drought tolerance in plant.

TABLE 5

Paraquat tolerance assay of OsDN-DTP1-transgenicrice plants at $T_2$ generation at transgenic event level ($1^{st}$ experiment)

| Event ID | Number of tolerant seedlings | Number of total seedlings | Tolerant rate (%) | P value | P ≤ 0.05 |
|---|---|---|---|---|---|
| DP0006.01 | 25 | 60 | 42 | 0.1793 | |
| DP0006.02 | 40 | 60 | 67 | 0.0456 | Y |
| DP0006.04 | 44 | 60 | 73 | 0.0048 | Y |
| DP0006.05 | 47 | 60 | 78 | 0.0007 | Y |
| DP0006.09 | 48 | 60 | 80 | 0.0004 | Y |
| DP0006.11 | 31 | 60 | 52 | 1.0000 | |
| DP0006.15 | 28 | 60 | 47 | 0.4987 | |
| DP0006.17 | 43 | 60 | 72 | 0.0087 | Y |
| DP0006.18 | 38 | 60 | 63 | 0.1172 | |
| DP0006.19 | 43 | 60 | 72 | 0.0087 | Y |
| ZH11-TC | 93 | 180 | 52 | | |

TABLE 6

Paraquat tolerance assay of OsDN-DTP1-transgenicrice plants at $T_2$ generation at transgenic event level ($2^{nd}$ experiment)

| Event ID | Number of tolerant seedlings | Number of total seedlings | Tolerant rate (%) | P value | P ≤ 0.05 |
|---|---|---|---|---|---|
| DP0006.05 | 32 | 60 | 53 | 0.0142 | Y |
| DP0006.09 | 45 | 60 | 75 | 0.0000 | Y |
| DP0006.11 | 14 | 60 | 23 | 0.0907 | |
| DP0006.12 | 40 | 60 | 67 | 0.0000 | Y |
| DP0006.14 | 13 | 24 | 54 | 0.0776 | |
| DP0006.15 | 27 | 60 | 45 | 0.1706 | |
| DP0006.17 | 23 | 60 | 38 | 0.6545 | |
| DP0006.18 | 32 | 60 | 53 | 0.0142 | Y |
| DP0006.19 | 32 | 60 | 53 | 0.0142 | Y |
| ZH11-TC | 76 | 216 | 35 | | |

Example 10

Transformation of *Arabidopsis* with OsDN-DTP1 Gene

To understand if OsDN-DTP1 gene can improve dicot plants' drought tolerance, or other traits, OsDN-DTP1 gene (vector DP0006) and empty vector DP0009 (VC) were transformed into *Arabidopsis* using floral dip method and transgenic plants were identified (Clough, S. T. and Bent, A. F. (1998) *The Plant Journal* 16, 735-743; Zhang, X. et al. (2006) *Nature Protocols* 1: 641-646).

To identify the transgenic progeny, the *Arabidopsis* seeds were surface-sterilized by first treating with 70% ethanol for 1 min and then with 50% bleach/50% water/0.05% Triton®X-100 for 8 min; rinsed in sterile water for three times until the water appeared clear and without any yellow color; and resuspended in sterile water and spreaded on selection plates containing appropriate antibiotics. The plates were dried until water dried up and seeds became stable on the plate. The seeds were vernalized by placing at 4° C. for 3 days; and then were moved to a growth chamber under long-day conditions. After growing on selection plates for 7-10 days, seedlings with healthy green cotyledons and true leaves and roots extend into the MS selection medium were considered as transformants. The transformants were then transplanted in trays filled with water-saturated soil, and the trays were moved to a growth chamber to allow plants grow under continuous light for seed collection. The transgenic plants were further confirmed by PCR analysis.

The expression levels of OsDN-DTP1 gene in transgenic *Arabidopsis* were analyzed by semi-quantitative PCR assay. The total RNA of the transformed *Arabidopsis* seedlings were extracted as described in example 7. The cDNA were obtained, actin gene was used as control, and DP0006-1 and DP0006-2 were used as primers for OsDN-DTP1 transgene. The primers for actin are listed as below:

```
actin-F:
                                             (SEQ ID NO: 17)
5'-AGGCACCTCTTAACCCTAAAGC-3' actin-R:
                                             (SEQ ID NO: 18)
5'-GGACAACGGAATCTCTCAGC-3'
```

PCR Reaction Mixture and Procedure:

| Reaction mix | (20 μL) |
| --- | --- |
| Template | 1 μL |
| Primers (10 μL) | each 0.5 μL |
| 2 × Taq MIX | 10 μL |
| ddH$_2$O | 8 μL |

PCR Cycle:

| | | |
| --- | --- | --- |
| 94° C. | 5 min | |
| 94° C. | 30 s | |
| 60° C. | 30 s | 27 cycles for actin gene, or 34 cycles for DTP1 transgene |
| 72° C. | 30 s | |
| 72° C. | 5 min | |

As shown in FIG. 3 A, OsDN-DTP1 transgene overexpressed in AtDP0006.06, AtDP0006.09, and AtDP0006.11. No detectable expression in the wild type and VC plants. The expression level in event AtDP0006.06 is significantly lower than that in event AtDP0006.09 and AtDP0006.11.

To characterize the performance of OsDN-DTP1-transgenic *Arabidopsis* plants under drought stress, wild-type (Columbia), VC plants (DP0009 transformant), and three AtDP0006 transgenic events were planted in planting soil to grow for 4 weeks under normal watering condition. The planting soils were watered to saturation before drought treatment, and the *Arabidopsis* plants grow without watering for about 12 days. When the relative water content of the soil decreased to about 3%, the *Arabidopsis* plants were re-watered for 3 days. Three measurements were performed and 12 plants were used. During drought treatment, the wilting levels of wild-type plants and VC plants were more apparent than those of the AtDP0006 events, and the transgenic AtDP0006 events grew better than the wild-type plants and VC plants at 3$^{rd}$ day after re-watering (FIG. 3C). After re-watering, more than 50% of transgenic plants survived, whereas the corresponding survival rates were less than 18% for wild-type plants and VC plants.

These results demonstrate that overexpression of OsDN-DTP1 transgene significantly enhanced drought tolerance in a dicot *Arabidopsis*. In addition, these results further show that a monocot gene (OsDN-DTP1 from rice) can function in a dicot plant (*Arabidopsis*).

What is claimed is:

1. A method of increasing drought tolerance in a plant, comprising: (a) expressing in a plant cell a polynucleotide operably linked to at least one heterologous regulatory element, wherein said polynucleotide encodes a polypeptide having an amino acid sequence of at least 99% sequence identity to SEQ ID NO: 4; and (b) obtaining a progeny plant, wherein the progeny plant comprises the polynucleotide operably linked to the at least one heterologous regulatory element in its genome and exhibits increased drought tolerance when compared to a control plant.

2. The method of claim 1, wherein the polypeptide comprises the amino acid sequence of SEQ ID NO: 4.

3. The method of claim 1, wherein said plant is selected from the group consisting of rice, maize, soybean, sunflower, sorghum, canola, wheat, alfalfa, cotton, barley, millet, sugarcane and switchgrass.

4. The method of claim 1, wherein the plant is a rice plant.

5. The method of claim 2, wherein the plant is a rice plant.

* * * * *

SEQUENCE LISTING

<160> NUMBER OF SEQ ID NOS: 18

<210> SEQ ID NO 1
<211> LENGTH: 626
<212> TYPE: DNA
<213> ORGANISM: Oryza sativa

<400> SEQUENCE: 1

```
agatctgagc agtctgaagt cccaatattg tctcaagaag actcttgatt acttgaagga      60
taattgaaac agcagctata gcaacataca ctccaataaa tagagatgga ttaaatggaa     120
tgctgcctga tgtttcatat gacagccaat agtcactagc catttcagta acttgccata     180
caattgcaaa agcaagcatg ccgacaaccc cccaccaacc ccaagcctct gtcatatata     240
acttgtacac acgccaactt acttgaccac tttctctttc ctcttctcgt ataattttag     300
aagtagctgc ttctatatca ggtgcaacaa gtaccttctc acccttcca atggatctag      360 agcgaagaga aggaattctg gctaccgcct taggctgaga atattcagtt ttgacaactt     420
gtcgactttg atccaccagt tccattgaac tatcatgagc agcaacaaga gctaagaaat     480
ctgagccagc atctagtaac tcatcatatt tccctgactg cacaatcatg ccatctctca     540
tgacctgcac aatcacatgg aaaaaatgat taaaaatcaa gtcaaggaca aaagtgtatg     600
ttctactccc tctgccctgt aatatg                                         626
```

<210> SEQ ID NO 2
<211> LENGTH: 398
<212> TYPE: DNA
<213> ORGANISM: Oryza sativa

<400> SEQUENCE: 2

-continued

```
tacattatta catatgttcc gttccagaaa aaaattcaaa cattatttat gcccaaagaa    60
aattaaacaa ccacaacgcg tatgcatatg cttgcatttg tttatactag ctcaactcct   120
ccaaagaaat catcatcatg catgcatgat atacaaacaa aaggttgcat tgcagctggt   180
aggctcatgg cttccggcga ccgccgccgc cgccgtggtc gtcgcacagg ccggcgtcga   240
gggtgtggta gttggcgtac cggctgggcg ccgacggcgg cacgcggaac ccctcggca    300 tgcacccgtt cgccgcccgc ccgcggaata cgccggcgg cggctgctgc cggcggtgcg    360
gcgacgacga ccgcgccctg aacggcacca gcaacgcc                           398
```

<210> SEQ ID NO 3
<211> LENGTH: 318
<212> TYPE: DNA
<213> ORGANISM: Oryza sativa

<400> SEQUENCE: 3

```
atgttccgtt ccagaaaaaa attcaaacat tatttatgcc caaagaaaat taaacaacca    60
caacgcgtat gcatatgctt gcatttgttt atactagctc aactcctcca agaaatcat   120 catcatgcat gcatgatata caaacaaaag gttgcattgc agctggtagg ctcatggctt   180
ccggcgaccg ccgccgccgc cgtggtcgtc gcacaggccg gcgtcgaggg tgtggtagtt   240
ggcgtaccgg ctgggcgccg acggcggcac gcggaacccc tcggcatgc acccgttcgc    300 cgcccgcccg cggaataa                                                 318
```

<210> SEQ ID NO 4
<211> LENGTH: 105
<212> TYPE: PRT
<213> ORGANISM: Oryza sativa

<400> SEQUENCE: 4

```
Met Phe Arg Ser Arg Lys Lys Phe Lys His Tyr Leu Cys Pro Lys Lys
1               5                   10                  15

Ile Lys Gln Pro Gln Arg Val Cys Ile Cys Leu His Leu Phe Ile Leu
            20                  25                  30

Ala Gln Leu Leu Gln Arg Asn His His His Ala Cys Met Ile Tyr Lys
        35                  40                  45

Gln Lys Val Ala Leu Gln Leu Val Gly Ser Trp Leu Pro Ala Thr Ala
    50                  55                  60

Ala Ala Ala Val Val Val Ala Gln Ala Gly Val Glu Gly Val Val Val
65                  70                  75                  80

Gly Val Pro Ala Gly Arg Arg Arg His Ala Glu Pro Pro Arg His
                85                  90                  95

Ala Pro Val Arg Arg Pro Pro Ala Glu
            100                 105
```

<210> SEQ ID NO 5
<211> LENGTH: 27
<212> TYPE: DNA
<213> ORGANISM: Artificial Sequence
<220> FEATURE:
<223> OTHER INFORMATION: synthesized

<400> SEQUENCE: 5

```
accccaggct ttacacttta tgcttcc                                        27
```

<210> SEQ ID NO 6
<211> LENGTH: 25
<212> TYPE: DNA

```
<213> ORGANISM: Artificial Sequence
<220> FEATURE:
<223> OTHER INFORMATION: synthesized

<400> SEQUENCE: 6
aacccactcg tgcacccaac tgatc                                          25

<210> SEQ ID NO 7
<211> LENGTH: 33
<212> TYPE: DNA
<213> ORGANISM: Artificial Sequence
<220> FEATURE:
<223> OTHER INFORMATION: synthesized

<400> SEQUENCE: 7
aaaggatcct acattattac atatgttccg ttc                                 33

<210> SEQ ID NO 8
<211> LENGTH: 21
<212> TYPE: DNA
<213> ORGANISM: Artificial Sequence
<220> FEATURE:
<223> OTHER INFORMATION: synthesized

<400> SEQUENCE: 8
ggcgttgctg gtgccgttca g                                              21

<210> SEQ ID NO 9
<211> LENGTH: 34
<212> TYPE: DNA
<213> ORGANISM: Artificial Sequence
<220> FEATURE:
<223> OTHER INFORMATION: synthesized

<400> SEQUENCE: 9
aagcttagag cagcttggca acatggtgga gcac                                34

<210> SEQ ID NO 10
<211> LENGTH: 28
<212> TYPE: DNA
<213> ORGANISM: Artificial Sequence
<220> FEATURE:
<223> OTHER INFORMATION: synthesized

<400> SEQUENCE: 10
ctgcagagag atagatttgt agagagag                                       28

<210> SEQ ID NO 11
<211> LENGTH: 71
<212> TYPE: DNA
<213> ORGANISM: Artificial Sequence
<220> FEATURE:
<223> OTHER INFORMATION: synthesized

<400> SEQUENCE: 11
ctgcagagat ctggtaccgg tcgccaccat ggaagtcgac gtttcttgtt tcttaagatt    60
gaatcctgtt g                                                         71

<210> SEQ ID NO 12
<211> LENGTH: 30
<212> TYPE: DNA
<213> ORGANISM: Artificial Sequence
<220> FEATURE:
<223> OTHER INFORMATION: synthesized

<400> SEQUENCE: 12
```

-continued

```
ggatcctcta gtcccgatct agtaacatag                              30

<210> SEQ ID NO 13
<211> LENGTH: 45
<212> TYPE: DNA
<213> ORGANISM: Artificial Sequence
<220> FEATURE:
<223> OTHER INFORMATION: synthesized

<400> SEQUENCE: 13
ccgggatcct cgcgagtcga cctccaagct gggccacaac tgaag             45

<210> SEQ ID NO 14
<211> LENGTH: 33
<212> TYPE: DNA
<213> ORGANISM: Artificial Sequence
<220> FEATURE:
<223> OTHER INFORMATION: synthesized

<400> SEQUENCE: 14
cgagaattct ctagtcccga tctagtaaca tag                          33

<210> SEQ ID NO 15
<211> LENGTH: 17
<212> TYPE: DNA
<213> ORGANISM: Artificial Sequence
<220> FEATURE:
<223> OTHER INFORMATION: synthesized

<400> SEQUENCE: 15
caaccacaac gcgtatg                                            17

<210> SEQ ID NO 16
<211> LENGTH: 17
<212> TYPE: DNA
<213> ORGANISM: Artificial Sequence
<220> FEATURE:
<223> OTHER INFORMATION: synthesized

<400> SEQUENCE: 16
cctaccagct gcaatgc                                            17

<210> SEQ ID NO 17
<211> LENGTH: 22
<212> TYPE: DNA
<213> ORGANISM: Artificial Sequence
<220> FEATURE:
<223> OTHER INFORMATION: synthesized

<400> SEQUENCE: 17
aggcacctct taaccctaaa gc                                      22

<210> SEQ ID NO 18
<211> LENGTH: 20
<212> TYPE: DNA
<213> ORGANISM: Artificial Sequence
<220> FEATURE:
<223> OTHER INFORMATION: synthesized

<400> SEQUENCE: 18
ggacaacgga atctctcagc                                         20
```